(12) United States Patent
Yamaguchi et al.

(10) Patent No.: US 8,633,356 B2
(45) Date of Patent: Jan. 21, 2014

(54) METHOD FOR CONTROLLING ROOT PARASITIC PLANTS

(75) Inventors: Shinjiro Yamaguchi, Kanagawa (JP); Mikihisa Umehara, Kanagawa (JP); Atsushi Hanada, Kanagawa (JP); Satoko Yoshida, Kanagawa (JP); Ken Shirasu, Kanagawa (JP)

(73) Assignee: Riken, Wako-Shi, Saitama (JP)

( * ) Notice: Subject to any disclaimer, the term of this patent is extended or adjusted under 35 U.S.C. 154(b) by 960 days.

(21) Appl. No.: 12/461,058

(22) Filed: Jul. 30, 2009

(65) Prior Publication Data

US 2010/0043101 A1 Feb. 18, 2010

Related U.S. Application Data

(60) Provisional application No. 61/129,960, filed on Aug. 1, 2008.

(51) Int. Cl.
*C12N 15/29* (2006.01)
*C12N 15/52* (2006.01)
*C12N 15/82* (2006.01)

(52) U.S. Cl.
USPC ............ 800/285; 800/265; 800/276; 800/279

(58) Field of Classification Search
USPC .................................. 800/265, 279, 276, 285
See application file for complete search history.

(56) References Cited

PUBLICATIONS

Bouwmeester, H. et al. Trends in Plant Science; available online Apr. 9, 2007, vol. 12, No. 5 pp. 225-230.*
Zou, J. et al. Plant J. 2006, vol. 48, pp. 687-696.*
Beveridge, C. A., et al., "Branching Mutant *rms-2* in *Pisum sativum*," Plant Physiol., vol. 104, pp. 953-959 (1994).
Beveridge, C. A., et al., "Branching in Pea," Plant Plysiol., vol. 110, pp. 859-865 (1996).
Beveridge, C. A., et al., "Auxin Inhibition of Decapitation-Induced Branching is Dependent on Graft-Transmissible Signals Regulated by Genes *Rms1* and *Rms2*," Plant Physiol,. vol. 123, pp. 689-697 (2000).
Johnson, X., et al., "Branching Genes are Conserved across Species. Genes Controlling a Novel Signal in Pea are Coregulated by Other Long-Distance Signals," Plant Physiol., vol. 142, pp. 1014-1026 (2006).
Stirnberg, P., et al., "*MAX1* and *MAX2* control shoot lateral branching in *Arabidopsis*," Development, vol. 129, pp. 1131-1141 (2002).
Sorefan, K., et al., "*MAX4* and *RMS1* are orthologous dioxygenase-like genes that regulate shoot branching in *Arabidopsis* and pea," Genes & Dev., vol. 17, pp. 1469-1474 (2003).
Booker, J., et al., "MAX3/CCD7 is a Carotenoid Cleavage Dioxygenase Required for the Synthesis of a Novel Plant Signaling Molecule," Curr. Biol., vol. 14, pp. 1232-1238 (2004).
Booker, J., et al., "*MAX1* Encodes a Cytochrome P450 Family Member that Acts Downstream of *MAX3/4* to Produce a Carotenoid-Derived Branch-Inhibiting Hormone," Develop. Cell, vol. 8, pp. 443-449 (2005).
Turnbull, C.G.N., et al., "Micrografting techniques for testing long-distance signalling in *Arabidopsis*," Plant J., vol. 32, pp. 255-262 (2002).
Snowden, K.C., et al., "The *Decreased apical dominance1/Petunia hybrida Carotenoid Cleavage Dioxygenase8* Gene Affects Branch Production and Plays a Role in Leaf Senescence, Root Growth, and Flower Development," Plant Cell, vol. 17, pp. 746-759 (2005).
Simons, J. L., et al., "Analysis of the *Decreased Apical Dominance* Genes of Petunia in the Control of Axillary Branching," Plant Physiol., vol. 143, pp. 697-706 (2007).
Ishikawa, S., et al., "Suppression of Tiller Bud Activity in Tillering Dwarf Mutants of Rice," Plant Cell Physiol., vol. 46, No. 1, pp. 79-86 (2005).
Zou, J., et al., "The rice *High-Tillering DWARF1* encoding an ortholog of *Arabidopsis MAX3* is required for negative regulation of the outgrowth of axillary buds," Plant J., vol. 48, pp. 687-696 (2006).
Arite, T., et al., "*DWARF10, an RMS1/MAX4/DAD1* ortholog, controls lateral bud outgrowth in rice," Plant J., vol. 51, pp. 1019-1029 (2007).
Ongaro, V., et al., "Hormonal control of shoot branching," J. Experim. Botany, vol. 59, No. 1, pp. 67-74 (2008).
Schwartz, S. H., et al., "The Biochemical Characterization of Two Carotenoid Cleavage Enzymes from *Arabidopsis* Indicates That a Carotenoid-derived Compound Inhibits Lateral Branching," J. Biol. Chem., vol. 279, No. 45, pp. 46940-46945 (2004).
Auldridge, M. E., "Characterization of three members of the *Arabidopsis* carotenoid cleavage dioxygenase family demonstrates the divergent roles of this multifunctional enzyme family," Plant J., vol. 45, pp. 982-993 (2006).
Lechner, E., et al., "F-box proteins everywhere," Curr. Opin. Plant Biol., vol. 9, pp. 631-638 (2006).
Cook, C. E., et al., "Germination Stimulants. II. The Structure of Strigol-A Potent Seed Germination Stimulant for Witchweed (*Striga lutea Lour.*)," J. Am. Chem. Soc., vol. 94, No. 17, pp. 6198-6199 (1972).
Humphrey, A. J., et al., "Strigol: Biogenesis and physiological activity," Phytochemistry, vol. 67, pp. 636-640 (2006).
Bouwmeester, H. J., et al., "Secondary metabolite signalling in host-parasitic plant interactions," Curr. Opin. Plant Biol., vol. 6, pp. 358-364 (2003).
Akiyama, K., et al., "Plant sesquiterpenes induce hyphal branching in arbuscular mycorrhizal fungi," Nature, vol. 435, No. 9, pp. 824-827 (2005).
Bradow, J. M., et al., "Germination Stimulation in wild Oats (*Avena fatua* L.) by Synthetic Strigol Analogs and Gibberellic Acid," J. Plant Growth Regul., vol. 9, pp. 35-41 (1990).

(Continued)

*Primary Examiner* — Russell Kallis
(74) *Attorney, Agent, or Firm* — Birch, Stewart, Kolasch & Birch, LLP.

(57) ABSTRACT

It is an objective to provide a method for controlling root parasitic plants. The present invention is directed to a method for protecting plants from root parasitic plants comprising regulating the activity of a protein associated with the strigolactone biosynthetic pathway (including the strigolactone biosynthetic and signalling pathway) in plants or expression of a gene encoding such a protein.

2 Claims, 9 Drawing Sheets
(4 of 9 Drawing Sheet(s) Filed in Color)

(56) References Cited

PUBLICATIONS

Bradow, J. M., et al., "Comparison of the Seed Germination Effects of Synthetic Analogs of Strigol, Gibberellic Acid, Cytokinins, and Other Plant Growth Regulators," J. Plant Growth Regul., vol. 7, pp. 227-239 (1988).

Goldwasser, Y., et al., "Production of Strigolactones by *Arabidopsis thaliana* responsible for *Orobanche aegyptiaca* seed germination," Plant Growth Regul., vol. 55, pp. 21-28 (2008).

Yoneyama, K., et al., "Strigolactones, host recognition signals for root parasitic plants and arbuscular mycorrhizal fungi, from Fabaceae plants," New Phytol., vol. 179, pp. 484-494 (2008).

Matusova, R., et al., "The Strigolactone Germination Stimulants of the Plant-Parasitic *Striga* and *Orobanche* spp. are Derived from the Carotenoid Pathway," Plant Physiol., vol. 139, pp. 920-934 (2005).

Lopez-Raez, J. A., et al., "Tomato strigolactones are derived from carotenoids and their biosynthesis is promoted by phosphate starvation," New Phytol., vol. 178, pp. 863-874 (2008).

Bouwmeester, J. J., et al., "Rhizosphere communication of plants, parasitic plants and AM fungi," Trends Plant Sci., vol. 12, No. 5, pp. 224-230 (2007).

Yoneyama, K., et al., "Nitrogen deficiency as well as phosphorus deficiency in sorghum promotes the production and exudation of 5-deoxystrigol, the host recognition signal for arbuscular mycorrhizal fungi and root parasites," Planta, vol. 227, pp. 125-132 (2007).

Yoneyama, K., et al., "Phosphorus deficiency in red clover promotes exudation of orobanchol, the signal for mycorrhizal symbionts and germination stimulant for root parasites," Planta, vol. 225, pp. 1031-1038 (2007).

Sugimoto, Y., et al., "Production of (+)-5-deoxystrigol by *Lotus japonicus* root culture," Phytochemistry, vol. 69, pp. 212-217 (2008).

Zou, J., et al., "Characterizations and fine mapping of a mutant gene for high tillering and dwarf in rice (*Oryza sativa* L.)," Planta, vol. 222, pp. 604-612 (2005).

Gressel, J., et al., "Major heretofore intractable biotic constraints to African food security that may be amenable to novel biotechnological solutions," Crop Prot., vol. 23, pp. 661-689 (2004).

Joel, D. M., "The long-term approach to parasitic weeds control: manipulation of specific developmental mechanisms of the parasite," Crop Prot., vol. 19, pp. 753-758 (2000).

Xie, X., et al., "2'-Epi-orobanchol and Solanacol, Two Unique Strigolactones, Germination Stimulants for Root Parasitic Weeds, Produced by Tobacco," J. Agric. Food Chem., vol. 55, pp. 8067-8072 (2007).

Cline, M. G., "Apical Dominance," The Botanical Review, vol. 57, No. 4, pp. 318-358 (1991).

Magome, H., et al., "*dwarf and delayed-flowering 1*, a novel *Arabidopsis* mutant deficient in gibberellin biosynthesis because of overexpression of a putative AP2 transcription factor," Plant J., vol. 37, pp. 720-729 (2004).

Kamachi, K., et al., "A Role for Glutamine Synthetase in the Remobilization of Leaf Nitrogen during Natural Senescence in Rice Leaves," Plant Physiol., vol. 96, pp. 411-417 (1991).

Murashige, T., et al., "A Revised Medium for Rapid Growth and Bio Assays with Tobacco Tissue Cultures," Physiol. Plant., vol. 15, pp. 473-497 (1962).

Noren, H., et al., "A convenient and versatile hydroponic cultivation system for *Arabidopsis thaliana*," Physiol. Plant., vol. 121, pp. 343-348 (2004).

Varbanova, M., et al., "Methylation of Gibberellins by *Arabidopsis* GAMT1 and GAMT2," Plant Cell, vol. 19, pp. 32-45 (2007).

Mangnus, E. M., et al., "Improved synthesis of strigol analog GR24 and evaluation of the biological activity of its diastereomers," J. Agric. Food Chem., vol. 40, No. 7, pp. 1230-1235 (1992).

Gurney, A. L., et al., "A novel form of resistance in rice to the angiosperm parasite *Striga hermonthica*," New Phytol., vol. 169, pp. 199-208 (2006).

Gomez-Roldan, V., et al., "Strigolactone inhibition of shoot branching," Nature, vol. 455, pp. 189-195 (2008).

Umehara, M., et al., "Inhibition of shoot branching by new terpenoid plant hormones," Nature, vol. 455, pp. 195-201 (2008).

\* cited by examiner

METHOD FOR CONTROLLING ROOT PARASITIC PLANTS

CROSS-REFERENCE TO RELATED APPLICATIONS

This application claims the benefit of U.S. Provisional Application No. 61/129,960 filed on Aug. 1, 2008.

BACKGROUND OF THE INVENTION

1. Field of the Invention

The present invention relates to a method for controlling root parasitic plants comprising regulating the activity of a protein associated with the strigolactone biosynthetic pathway (including the strigolactone biosynthetic and signalling pathway) or expression of a gene encoding such a protein.

2. Background Art

Damage to agricultural crops caused by root parasitic plants (or root parasitic weeds), such as *Striga* or *Orobanche* species, is a global-scale problem in recent years. In Africa, in particular, two-thirds of cereal growing areas are damaged by *Striga* (mainly *Striga hermonthica*), and such damage affects food supply to as many as 300 million people.

Root parasitic plants develop an organ that is referred to as the haustorium after germination and they grow by taking roots of host plants and depriving them of nutrients or moisture. Seed germination of root parasitic plants in the soil is induced by strigolactone, which is a germination stimulant released from the root of the host plant. This is considered to be deeply involved in the survival strategy of root parasitic plants, which experience selective germination of seeds distributed in the vicinity of the root of the host plant (i.e., a radical can reach the root of the host plant after germination).

Recently, strigolactone was demonstrated to be a substance that is essential for host recognition of symbiotic arbuscular mycorrhizal fungi (AM fungi). Specifically, root parasitic plants are considered to utilize strigolactone that a plant originally releases for AM fungi to search for the root of a host plant.

Establishment of an effective method for avoiding or controlling root parasitic plants is a highly important and urgent global-scale objective, although no effective method has yet been developed.

SUMMARY OF THE INVENTION

The present inventors found plants having a high capacity for strigolactone production and plants having a low capacity therefor among rice and *Arabidopsis thaliana* mutants. The present inventors found that *Striga* seed germination-stimulating activity would significantly change in root exudates of such plants. Accordingly, use of such plants to control root parasitic plants is considered to reduce damage to agricultural crops.

The present inventors found that plants to be regulated or plants other than those to be regulated could be protected from root parasitic plants by regulating the activity of proteins associated with the strigolactone biosynthetic pathway (including the strigolactone biosynthetic and signalling pathway) or expression of a gene encoding such a protein, based on the above findings. This has led to the completion of the present invention.

Specifically, the present invention relates to a method for protecting plants from root parasitic plants comprising regulating the activity of a protein associated with the strigolactone biosynthetic or signalling pathway in plants or expression of a gene encoding such a protein. Examples of genes encoding proteins associated with the strigolactone biosynthetic or signalling pathway include a gene encoding a carotenoid cleavage dioxygenase or cytochrome P450 oxidase and a gene encoding a member of the F-box leucine-rich repeat (LRR) protein family.

BRIEF DESCRIPTION OF THE DRAWINGS

The patent or application file contains at least one drawing executed in color. Copies of this patent or patent application publication with color drawing(s) will be provided by the office upon request and payment of the necessary fee.

[M+H]$^+$ (m/z 347) was selected as a parent ion on quadrapole MS and [M+H-142]$^+$ (m/z 205.1) and [M+H-250]$^+$ (m/z 97.0) were detected as fragment ions on time-of-flight MS. These ion transitions were detectable in root exudates of segregated wild type (D10 D10) and heterozygotes (D10 d10-2), but not in those of d10-2 homozygotes. In root exudates of Shiokari seedlings, epi-5DS was the only strigolactone detectable by LC-MS/MS analysis. However, in our previous survey of known strigolactones using Nipponbare seedlings, we detected 2'-epi-orobanchol (or its isomer) in addition to epi-5DS. We therefore used the d10-2 allele in the Nipponbare background to see if the content of 2'-epi-orobanchol (or its isomer) is reduced by the d10 mutation. Because homozygous d10-2 mutant plants were nearly sterile in our growth condition, we used progenies of heterozygotes (D10 d10-2) for this experiment. Consistent with the previous notion, we were able to detect a mono-hydroxylated form of epi-5DS (tentatively identified as 2'-epi-orobanchol or its isomer) in root exudates from the wild type and the heterozygote, but not in exudates from the homozygous d10-2 mutant. These data provide evidence that overall strigolactone levels are decreased in root exudates of d10 seedlings.

Figure 9:
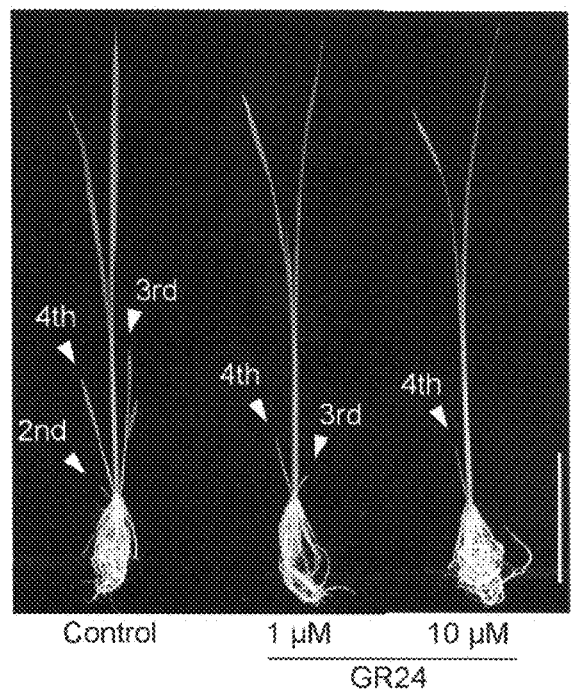
Figure 9:
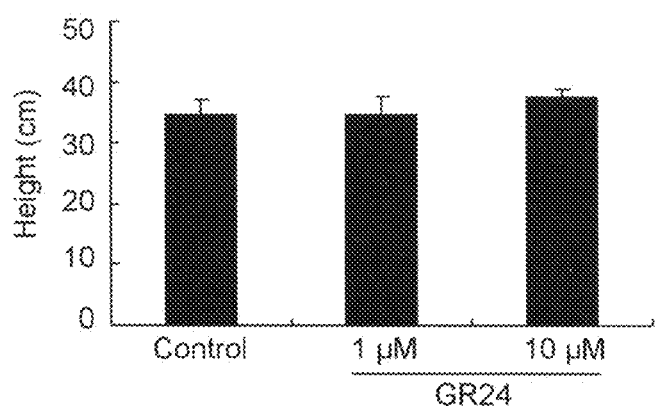
Figure 9:
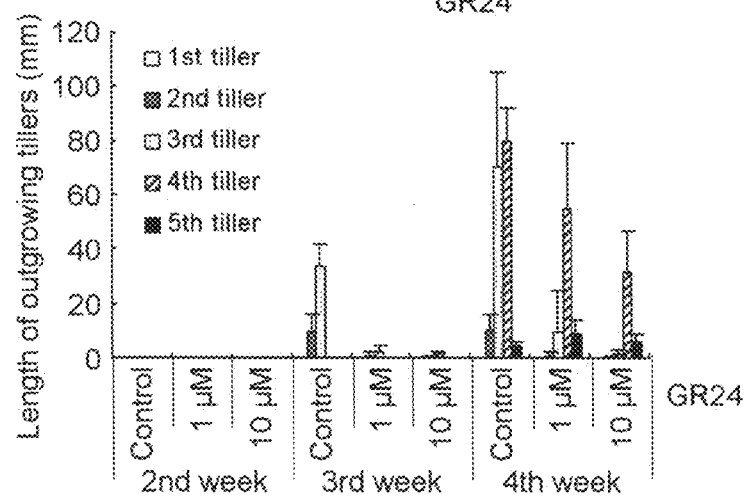

FIG. 9 shows the effect of GR24 on tiller growth of wild type seedlings. a: Four-week-old wild type seedlings grown hydroponically in the presence or absence of GR24 in the culture media. Arrowheads indicate outgrowth of tillers. The 5th tiller is not visible as it is enclosed by the leaf sheath. Bar is 10 cm. b and c: GR24 treatment inhibited the growth of tillers (b), but did not change the plant height (c). Data are the means+s.d. (n=8).

PREFERRED EMBODIMENTS OF THE INVENTION

Hereafter, the present invention will be described in detail.

The present invention relates to a method for protecting plants, such as agricultural crops, from root parasitic plants by regulating the activity of a protein associated with the strigolactone biosynthetic pathway (including the strigolactone biosynthetic and signalling pathway) in plants or expression of a gene encoding such a protein to regulate strigolactone in root exudates.

Figure 1:
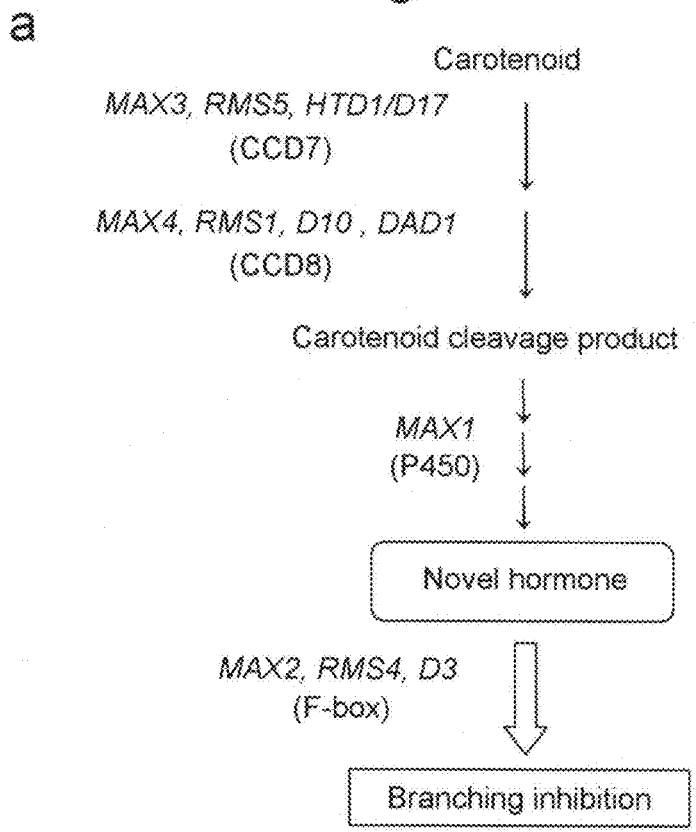
FIG. 1 shows the novel branching inhibitor pathway (a) and chemical structures of representative strigolactones (b).
Figure 1:
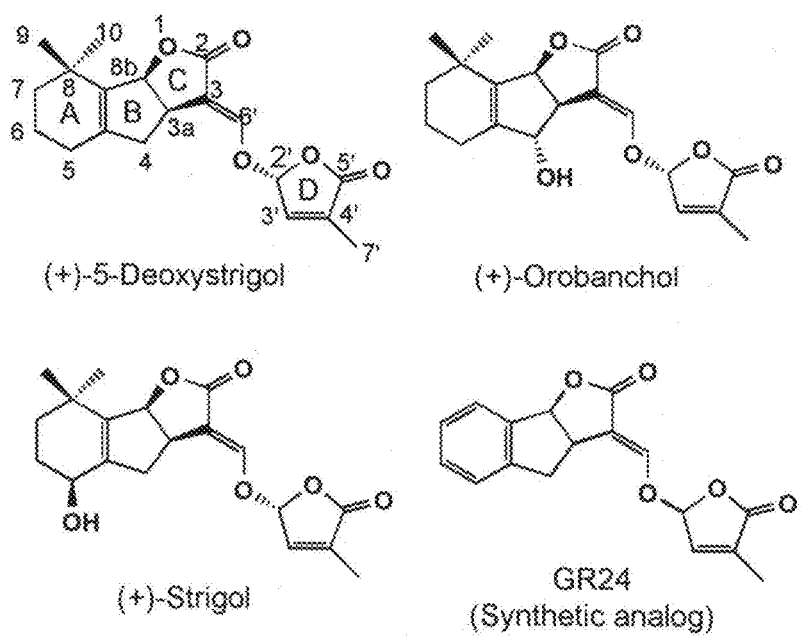

Representative examples of strigolactone include (+)-5-Deoxystrigol (5DS), (+)-Orobanchol and (+)-Strigol as shown in FIG. 1b.

The term "strigolactone biosynthetic and signalling pathway" used herein refers to a biosynthetic pathway from carotenoid to strigolactone and a signalling pathway subsequent to strigolactone. As shown in FIG. 1a, the activity of a carotenoid cleavage dioxygenase or cytochrome P450 oxidase associated with the biosynthetic pathway from carotenoid to strigolactone ("novel hormone" in FIG. 1a) or expression of genes encoding such enzymes may be lowered or deleted, so as to lower strigolactone expression. Along with such lowered strigolactone expression, the strigolactone content in plant root exudates is lowered. This can prevent induction of seed germination of root parasitic plants and can protect plants from root parasitic plants. If, as compared with a wild type plant, the activity of a carotenoid cleavage dioxygenase or cytochrome P450 oxidase or the expression of genes encoding such enzymes is significantly lowered (for example, by 50%, 60%, 70%, 80%, 90% or 100%) in an altered plant, the altered plant would be protected effectively from root parasitic plants.

When the activity of a carotenoid cleavage dioxygenase and a cytochrome P450 oxidase or expression of genes encoding such enzymes is increased, strigolactone levels are elevated. Along with the elevated strigolactone expression, the strigolactone content in plant root exudates is increased. Seed germination of root parasitic plants is highly induced in the vicinity of the plant in which the strigolactone content is increased. Therefore, these plants can be used as trap plants to remove seeds of root parasitic plants in the soil, and can in turn protect other plants from root parasitic plants. If, as compared with a wild type plant, the activity of a carotenoid cleavage dioxygenase or cytochrome P450 oxidase or the expression of genes encoding such enzymes is significantly elevated (for example, by 50%, 60%, 70%, 80%, 90%, 100% or more) in an altered plant, it would be effective to use the altered plant as trap plants.

Also, as shown in FIG. 1a, the activity of a member of the F-box leucine-rich repeat (LRR) protein family associated with the signalling pathway subsequent to strigolactone (hereafter merely referred to as the "F-box protein") or expression of a gene encoding such a protein may be lowered or deleted. This would prevent the pathway subsequent to strigolactone from advancing, which in turn would result in increased strigolactone content in plant root exudates. The increased strigolactone content in plant root exudates can result in induction of seed germination of root parasitic plants in the vicinity of the plants of interest and protection of other plants from root parasitic plants. If, as compared with a wild type plant, the activity of the F-box protein or the expression of a gene encoding such a protein is significantly lowered (for example, by 50%, 60%, 70%, 80%, 90%, or 100%) in an altered plant, it would be effective to use the altered plant as trap plants.

When the activity of the F-box protein or expression of a gene encoding such a protein is increased, the strigolactone signalling pathway advances, which in turn results in decreased strigolactone content in plant root exudates. The decreased strigolactone content in plant root exudates can prevent induction of seed germination of root parasitic plants, and the plants of interest can be protected from root parasitic plants. If, as compared with a wild type plant, the activity of the F-box protein or the expression of a gene encoding such a protein is significantly elevated (for example, by 50%, 60%, 70%, 80%, 90%, 100% or more) in an altered plant, the altered plant would be protected effectively from root parasitic plants.

The term "carotenoid cleavage dioxygenase" used herein refers to an enzyme that oxidatively cleaves a double bond of a carotenoid or an apocarotenoid to give products with a ketone or an aldehyde group at the cleavage site. Examples of genes encoding a carotenoid cleavage dioxygenase include genes encoding rice (*Oryza sativa*)-derived carotenoid cleavage dioxygenase (CCD)$_7$ (genome DNA: SEQ ID NO: 1; amino acid sequence: SEQ ID NO: 2), *Arabidopsis thaliana*-derived CCD7 (genome DNA: SEQ ID NO: 3; amino acid sequence: SEQ ID NO: 4), *Oryza sativa*-derived CCD8 (genome DNA: SEQ ID NO: 5; amino acid sequence: SEQ ID NO: 6), and *Arabidopsis thaliana*-derived CCD8 (genome DNA: SEQ ID NO: 7; amino acid sequence: SEQ ID NO: 8).

The term "cytochrome P450 oxidase" used herein refers to an enzyme that catalyzes an insertion of an oxygen atom into a substrate. An example of a gene encoding a cytochrome P450 oxidase is a gene encoding CYP711A1, and more specifically, an example of a gene encoding CYP711A1 is a gene encoding *Arabidopsis thaliana*-derived CYP711A1 (genome DNA: SEQ ID NO: 9; amino acid sequence: SEQ ID NO: 10).

The term "F-box protein" used herein refers to one of the three components of the SCF complex (the Skp, Cullin, F-box containing complex), which mediates ubiquitination of a target protein for degradation by the proteasome and is involved in signal perception or transduction. In the SCF complex, F-box protein is responsible for the recognition of the target protein. Examples of genes encoding the F-box protein include genes encoding the *Oryza sativa*-derived F-box protein (genome DNA: SEQ ID NO: 11; amino acid sequence: SEQ ID NO: 12) and the *Arabidopsis thaliana*-derived F-box protein (genome DNA: SEQ ID NO: 13; amino acid sequence: SEQ ID NO: 14).

In the present invention, genes encoding a carotenoid cleavage dioxygenase, a cytochrome P450 oxidase, and the F-box protein are not limited to genes consisting of the nucleotide sequences as shown in the above SEQ ID NOs. Examples of such genes include mutants of the above genes and homologous genes of the above genes derived from other plant species. Examples of such mutants and such homologous genes derived from other plant species include: (1) a gene consisting of a nucleotide sequence derived from any of the nucleotide sequences as shown in the above SEQ ID NOs by deletion, substitution, and/or addition of 1 or several (e.g., 1 to 10 or 1 to 5) nucleotides and encoding a protein having activity of the original proteins encoded by the nucleotide sequences as shown in the above SEQ ID NOs; (2) a gene hybridizing under stringent conditions to DNA complementary to any of the nucleotide sequences as shown in the above SEQ ID NOs and encoding a protein having activity of the original proteins encoded by the nucleotide sequences as shown in the above SEQ ID NOs; and (3) a gene consisting of a nucleotide sequence having at least 70%, 80%, 85%, 90%, 95%, 96%, 97%, 98%, or 99% or more sequence identity to any of the nucleotide sequences as shown in the above SEQ ID NOs and encoding a protein having activity of the original proteins encoded by the nucleotide sequences as shown in the above SEQ ID NOs.

Under stringent conditions, hybridization is carried out with the use of, for example, $^{32}$P-labeled probe DNA in a hybridization solution comprising 5×SSC (0.75 M NaCl and 0.75 M sodium citrate), 5×Denhardt's reagent (0.1% Ficoll, 0.1% polyvinyl pyrrolidone, and 0.1% bovine serum albumin), and 0.1% sodium dodecyl sulfate (SDS) at 45° C. to 65° C., and preferably at 55° C. to 65° C. A step of washing is carried out with a washing solution comprising 2×SSC and 0.1% SDS at 45° C. to 55° C., and more preferably with a washing solution comprising 0.1×SSC and 0.1% SDS at 45° C. to 55° C.

Examples of plants to be protected from root parasitic plants include agricultural crops, such as rice (*Oryza sativa*), maize (*Zea mays*), cowpea (*Vigna ungliculata*), sorghum (*Sorghum bicolor*), and tomato (*Solanum lycopersicum*).

Examples of root parasitic plants include *Striga* (e.g., *Striga hermonthica*) and *Orobanche* species.

In the present invention, examples of methods for lowering or deleting expression of genes encoding a protein associated with the strigolactone biosynthetic or signalling pathway include a method comprising introducing a mutation into the gene, a method comprising deleting the gene, and a method comprising inhibiting translation of mRNA of the gene to a protein with the use of antisense oligonucleotide.

In the present invention, an example of a method for enhancing expression of genes encoding a protein associated with the strigolactone biosynthetic or signalling pathway is a method comprising introducing the gene of interest into a plant to overexpress a gene therein.

In the present invention, an example of a method for enhancing the activity of a protein associated with the strigolactone biosynthetic or signalling pathway is a method involving the use of an agonist against the protein.

In the present invention, examples of methods for lowering or deleting the activity of a protein associated with the strigolactone biosynthetic or signalling pathway include a method of using an antagonist against the protein to lower or delete activity and a method of using a neutralizing antibody against the protein to lower or delete activity.

EXAMPLES

The present invention is hereafter described in greater detail with reference to the following examples, although the technical scope of the present invention is not limited thereto.

Introduction

Shoot branching involves the formation of axillary buds in the axil of leaves and subsequent outgrowth of the buds. Previous studies have suggested the involvement of a novel, as yet unidentified, hormone in inhibiting outgrowth of axillary buds, using a series of recessive mutants that exhibit enhanced shoot branching. These mutants include ramosus (rms) of pea (*Pisum sativum*)[1-4], more axillary growth (max) of *Arabidopsis*[5-9], decreased apical dominance (dad) of petunia (*Petunia hybrida*)[10,11] and dwarf (d) or high-tillering dwarf (htd) of rice (*Oryza sativa*)[12-14]. Reciprocal grafting experiments, double mutant analysis and cloning of these genetic loci suggested that the novel hormone is biosynthesized from carotenoids and moves acropetally to inhibit axillary bud outgrowth[15]. In the proposed biosynthesis pathway, MAX3, RMS5 and HTD1/D17 encode carotenoid cleavage dioxygenase 7 (CCD7)[4,7,13], while MAX4, RMS1, D10 and DAD1 encode another subclass of CCDs designated as CCD8[6,10,14] (FIG. 1a). CCD7 and CCD8 might catalyze sequential carotenoid cleavage reactions, although their endogenous substrates and exact enzymatic function in plants have not been conclusive[7,16,17]. MAX1 is a cytochrome P450 monooxygenase presumably involved in a later biosynthetic step[8] (FIG. 1a). Unlike the biosynthetic mutants, the branching phenotype of the max2, rms4 and dad2 mutants is not rescued by grafting onto a wild type rootstock, suggesting that they are insensitive to the branch-inhibiting hormone[2,8,11] MAX2, RMS4 and D3 are orthologous members of the F-box leucine-rich repeat (LRR) protein family[4,5,12] (FIG. 1a), which probably act as the substrate recognition subunit of SCF ubiquitin E3 ligase for proteasome-mediated proteolysis[18]. The predicted biochemical function of MAX2, RMS4 and D3 is consistent with their role in signal transduction of the novel hormone.

Strigolactones are a group of terpenoid lactones (FIG. 1b), which have been found in root exudates of diverse plant species and were initially characterized as seed germination stimulants of root parasitic plants such as *Striga* and *Orobanche* species[19-21] More recently, strigolactones were shown to act as root-derived signals for symbiotic interaction with arbuscular mycorrhizal (AM) fungi[22], which facilitate the uptake of soil nutrients by plants. This symbiosis is observed in more than 80% of terrestrial plants, coinciding with the wide distribution of this class of terpenes. Strigolactones may have additional unidentified function(s) in plants, because they induce seed germination of non-parasitic plants as well[23,24] and are also produced by non-hosts of AM fungi, including Arabidopsis[25,26] Little is known about the biosynthesis of strigolactones. Recent works have indicated that the ABC part (FIG. 1b) is derived from carotenoids, presumably via the formation of oxidatively cleaved product(s)[20,27,28] Taken together, current lines of evidence suggest that strigolactone biosynthesis involves a (epoxy)carotenoid cleavage enzyme conserved across diverse plant species. Although CCD7 and CCD8 encoded by the MAX/RMS/DAD/D loci fulfill these criteria[29], their role in strigolactone biosynthesis had not been examined. Therefore, we set out to examine whether the carotenoid-derived branching inhibitor shares its biosynthetic pathway with strigolactones using rice d mutants.

Materials and Methods
Plant Materials

Figure 6:
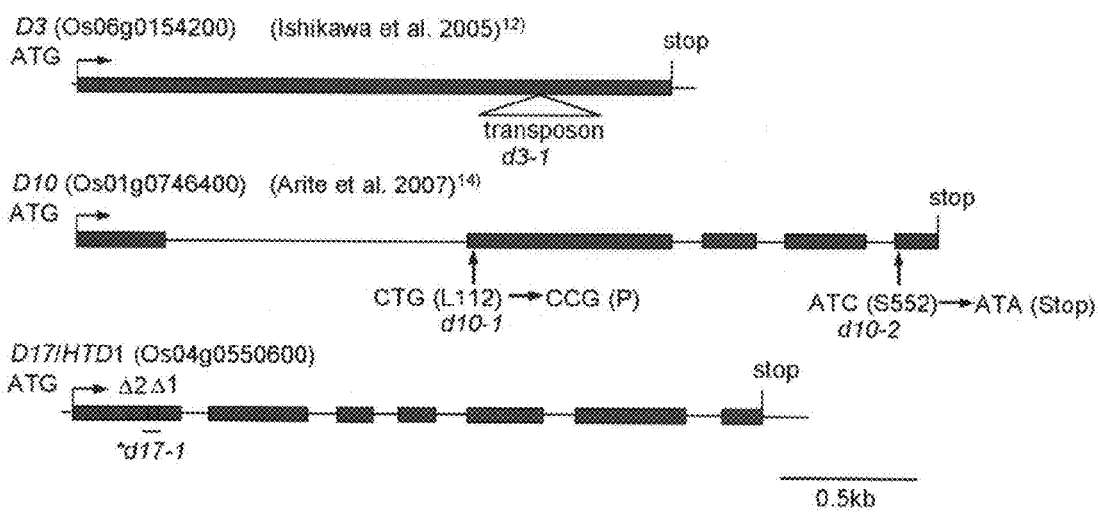
FIG. 6 shows rice and *Arabidopsis* branching mutants as used. Black boxes indicate exons. *New mutant alleles identified. (a) Rice mutants in the Shiokari background (d3-1, d10-1 and d17-1) and the Nipponbare background (d10-2). (b) *Arabidopsis* mutants (Col-0 background).
Figure 6:
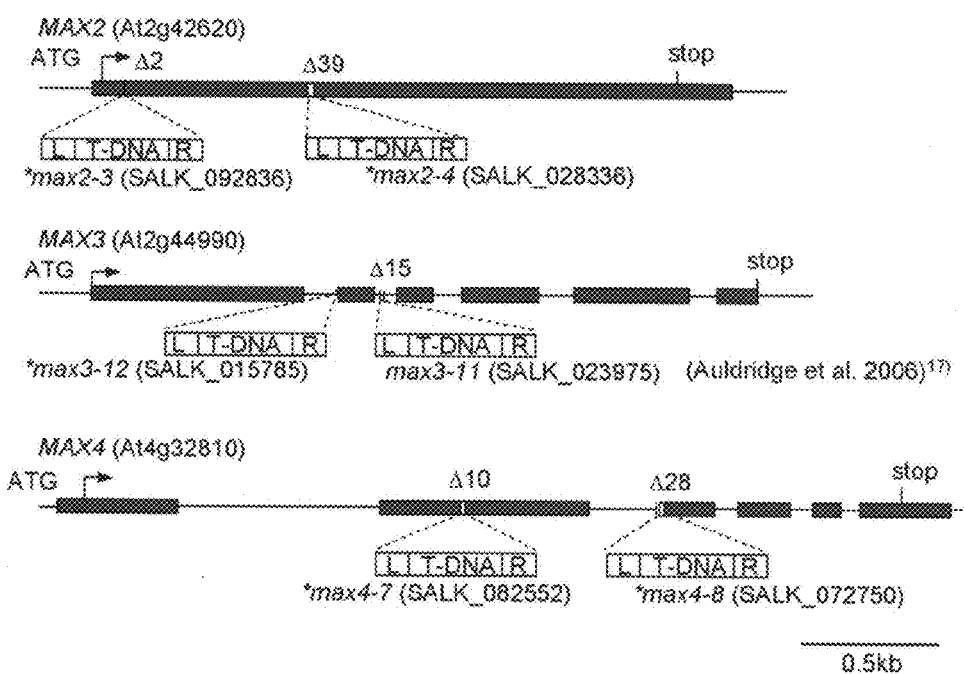

Rice and Arabidopsis mutants as used are shown in FIG. 6. Mutations in new mutant alleles used for this study were determined by DNA sequencing. Genotyping was carried out by PCR-based method using the primers listed in the following Table 1.

hydroponic culture media[39] solidified with 0.6% agar (pH5.7) and cultured at 25° C. under fluorescence white light (150-200 $\mu$mol m$^{-2}$ s$^{-1}$) with a 16 h light/8 h dark photoperiod for 5 days. Each seedling was then transferred to a glass vial containing a sterilized hydroponic culture solution (13 ml), fixed with a piece of sponge at the root-shoot junction to the top of the vial, and grown under the same condition for additional 7 days (total 2 weeks). The hydroponic solution was supplemented every 3 days. For large-scale cultures, the 2-weeks-old seedlings were transferred into a 4-L porcelain pot containing the same hydroponic solution and grown under the same condition. After the transfer to pots, the solution was renewed weekly.

Arabidopsis Hydroponic Culture

We used Arabidopsis thaliana ecotype Col-0 as the wild type and max mutants (FIG. 6). Seeds were sterilized in 1% sodium hypochlorite solution for 5 min, rinsed with sterile water, and stratified for one day at 4° C. The seeds were placed on the half strength Murashige and Skoog (MS) medium[40] containing 1% sucrose and 0.8% agar (pH5.7) at 22° C. under fluorescence white light (60-70 $\mu$mol m$^{-2}$ s$^{-1}$) with a 16 h light/8 h dark photoperiod for 15 days. Plants were then transferred to a glass pot containing 400 ml hydroponic solution[41] and grown under the same environmental conditions

TABLE 1

Table 1: List of primers used for genotyping and qRT-PCR.

| genotyping | allele | Oligomer* | 5'-sequence-3' | SEQ ID NO. |
|---|---|---|---|---|
| rice | d10-2 | F | TTGGCTTTGCCTCGTTTC | SEQ ID NO. 15 |
| | | R | AGCCTCCACTTGTACTGTG | SEQ ID NO. 16 |
| Arabidopsis | max2-3, max2-4 | F | ACTCTCTCCGACCTCCCTGACG | SEQ ID NO. 17 |
| | | R | AAACACCTTGGAACTGTCCTAGC | SEQ ID NO. 18 |
| | max3-11, max3-12 | F | TGAGACTAGAGAGGATAACGGC | SEQ ID NO. 19 |
| | | R | AACATCTCTCCACCGAAACCGC | SEQ ID NO. 20 |
| | max4-7 | F | CTTAGGTTAGTACACCATGTTCG | SEQ ID NO. 21 |
| | | R | GTCTCCGTCACTATCGGATGCGC | SEQ ID NO. 22 |
| | max4-8 | F | CATGTCATGTCCAAACTCACCG | SEQ ID NO. 23 |
| | | R | AGTTTCCCGTATTTGCTCCCG | SEQ ID NO. 24 |
| qRT-PCR | gene | Oligomer* | 5'-sequence-3' | |
| rice | D10 | F | CTGTACAAGTTCGAGTGGCACC | SEQ ID NO. 25 |
| | | R | CCTCGTCCGTCTCCTCGTAC | SEQ ID NO. 26 |
| | | T | f-CAAGGCCAGCGGCAAGATTG-t** | SEQ ID NO. 27 |
| | Ubiquitin | F | AAGGTCACCAGGCTCAGGAAG | SEQ ID NO. 28 |
| | | R | GATCGAAGTGGTTGGCCATG | SEQ ID NO. 29 |
| | | T | f-CAACAACGACTGCGGCGCG-t** | SEQ ID NO. 30 |

*F, R and T respectively indicate forward, reverse (primers) and TaqMan probes.
**f and t respectively indicate the fluorescence labels, FAM and TAMRA.

Growth Conditions and Strigolactone Treatment

Rice and Arabidopsis seeds were surface-sterilized and the seedlings were first grown aseptically on agar media. Plants were then grown hydroponically in growth chambers. For both rice and Arabidopsis, strigolactones were added to the hydroponic culture medium.

Rice Hydroponic Culture

We used rice normal cultivars (Oryza sativa L. cv. Shiokari and cv. Nipponbare) and tillering dwarf mutants (FIG. 6) in this study. Rice seeds were washed in 70% ethanol for 30 sec, sterilized in 2.5% sodium hypochlorite solution for 15 min, rinsed with sterile water, and then imbibed at 28° C. in the dark for 2 days. Germinated seeds were transferred into tion for additional 15 days. The solution was renewed every 3 days. To measure germination stimulants, sterilized and stratified seeds were placed on glass beads (30 ml) wetted with $\frac{1}{10}$ strength MS liquid media (10 ml) in a Petri dish (9 cm diameter) and grown for 14 days under the same conditions above. The culture media were collected and subjected to S. hermonthica germination assay.

Strigolactone Analysis

The levels of strigolactones released to hydroponic culture media were estimated by germination stimulating activity using S. hermonthica seeds as described previously[32] Strigolactones were identified and quantified on LC-MS/MS by comparing the retention time and full-scan spectrum with those of authentic standards. We synthesized deuterium-labeled epi-5DS ($d_1$-epi-5DS) and used as an internal standard for quantitative analysis using LC-MS/MS.

LC-MS/MS Analysis

The hydroponic culture media were collected and extracted with ethyl acetate twice after adding $d_1$-epi-5DS as an internal standard. The ethyl acetate phase was concentrated in vacuo after drying over sodium sulfate. The roots were homogenized in acetone containing $d_1$-epi-5DS. The filtrates were dried up under nitrogen gas and dissolved in 10% acetone. The extracts were loaded onto Oasis HLB 3 ml cartridges (Waters, USA) and eluted with acetone after washing with de-ionized water. The eluates were loaded onto Seppak Silica 1 ml cartridges (Waters, USA), washed with ethyl acetate:n-hexane (15:85) and then eluted with ethyl acetate: n-hexane (35:65). The epi-5DS-containing fractions from culture media and roots were dissolved in 50% acetonitrile and subjected to LC-MS/MS analysis using a system consisting of a quadrupole/time-of-flight tandem mass spectrometer (Q-T of Premier; Waters) and an Acquity Ultra Performance liquid chromatograph (Waters) equipped with a reverse-phase column (Acquity UPLC BEH-$C_{18}$, 2.1×50 mm, 1.7 µm; Waters). The mobile phase was changed from 30% acetonitrile containing 0.05% acetic acid to 40% and 70% in 5 and 10 min after the injection, respectively, at a flow rate of 0.2 ml $min^{-1}$. Data analysis was performed as we described previously for gibberellin analysis using a MassLynx software (v. 4.1)[42].

Chemicals

Figure 7:
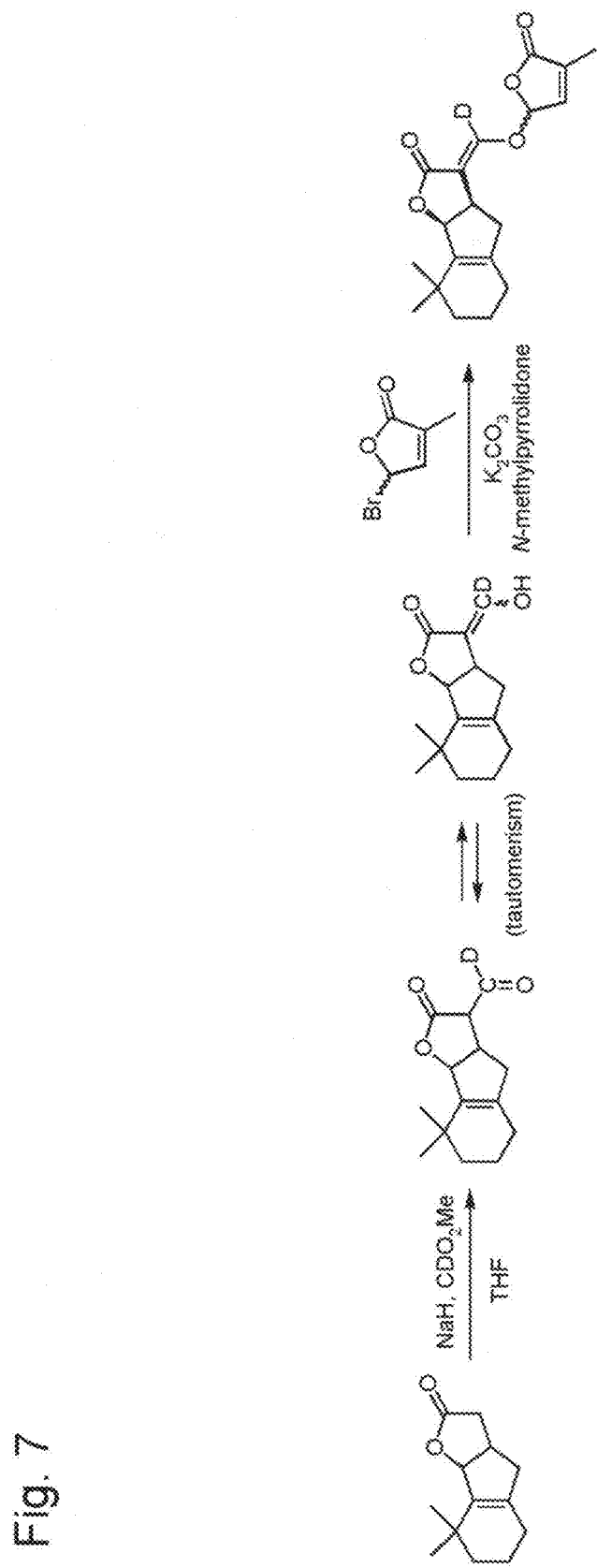
FIG. 7 shows a scheme for the synthesis of($\pm$)-[6'-$d_1$]-5DS. "CDO$_2$Me" indicates deuterium-labeled methyl formate.

GR24, 5DS and 5DS isomers were synthesized as described previously[22,43] (+)-Strigol and 2'-epi-orobanchol were provided by Dr. Kenji Mori (Emeritus Prof. of The University of Tokyo). For experiments in FIG. 3h, we used (+)-GR24 (courtesy of Prof. Peter McCourt (University of Toronto)). The synthesis of $d_1$-(epi)-5DS was carried out as described previously for non-labeled 5DS[22] The ABC ring was formylated with deuterium-labeled methyl formate and the following alkylation with racemic 4-bromo-2-methyl-2-buten-4-olide provided [6'-d]-5DS and its 2'-epimer (FIG. 7). (±)-[6'-$d_1$]-epi-5DS was purified by a silica gel column (Wakogel C-200, Wako Pure Industries; n-hexane-ethyl acetate stepwise) and semipreparative HPLC on reverse-(Inertsil ODS-3, GL Sciences; 70% acetonitrile in water) and normal-phase (Inertsil SIL-100A, GL Sciences; 15% ethanol in n-hexane) columns.

Germination Assay

Germination assays using *S. hermonthica* were performed as described previously[32] For each bioassay, de-ionized water and (+)-strigol solution were used as negative and positive controls, respectively.

Gene Expression Analysis

We performed quantitative reverse transcription-PCR (qRT-PCR) to determine D10 transcript levels, according to the method described before[38]. Total RNA was extracted from roots using RNeasy Maxi kit (Qiagen). qRT-PCR was carried out to determine D10 transcript levels using gene specific primers and a Taq-Man probe (Table 1 as describe above). Ubiquitin expression was used as an internal standard.

*S. hermonthica* Infection Assay

*S. hermonthica* infections were analysed using a rhizotron system as described by Gurney et al.[44], with slight modifications. Briefly, 1-week-old rice seedlings were transferred to root-observing rhizotron chambers (225 mm×225 mm petridish filled with rockwool and nylon mesh) supplied with 50 ml half-strength MS media, and grown for 2 weeks in a green house with a 12-h photoperiod (170-450 µmol $m^{-2}$ $s^{-1}$) at day/night temperature cycles of 28° C./20° C. *S. hermonthica* seeds were preconditioned on moist glass fibre filter papers (GF/A, Wattman) at 26° C. in dark for 2 weeks, and treated with or without $10^{-9}$ M (+)-strigol for 5 h in the dark. After rinsing with excess water, approximately 50 parasite seeds were carefully placed along rice roots and the rhizotrons were incubated under the same growth condition described above. The status of germination, infection and development of *S. hermonthica* were evaluated after 2 and 4 weeks of co-cultivation.

Results

Strigolactone Levels in Rice d Mutants

Figure 2:
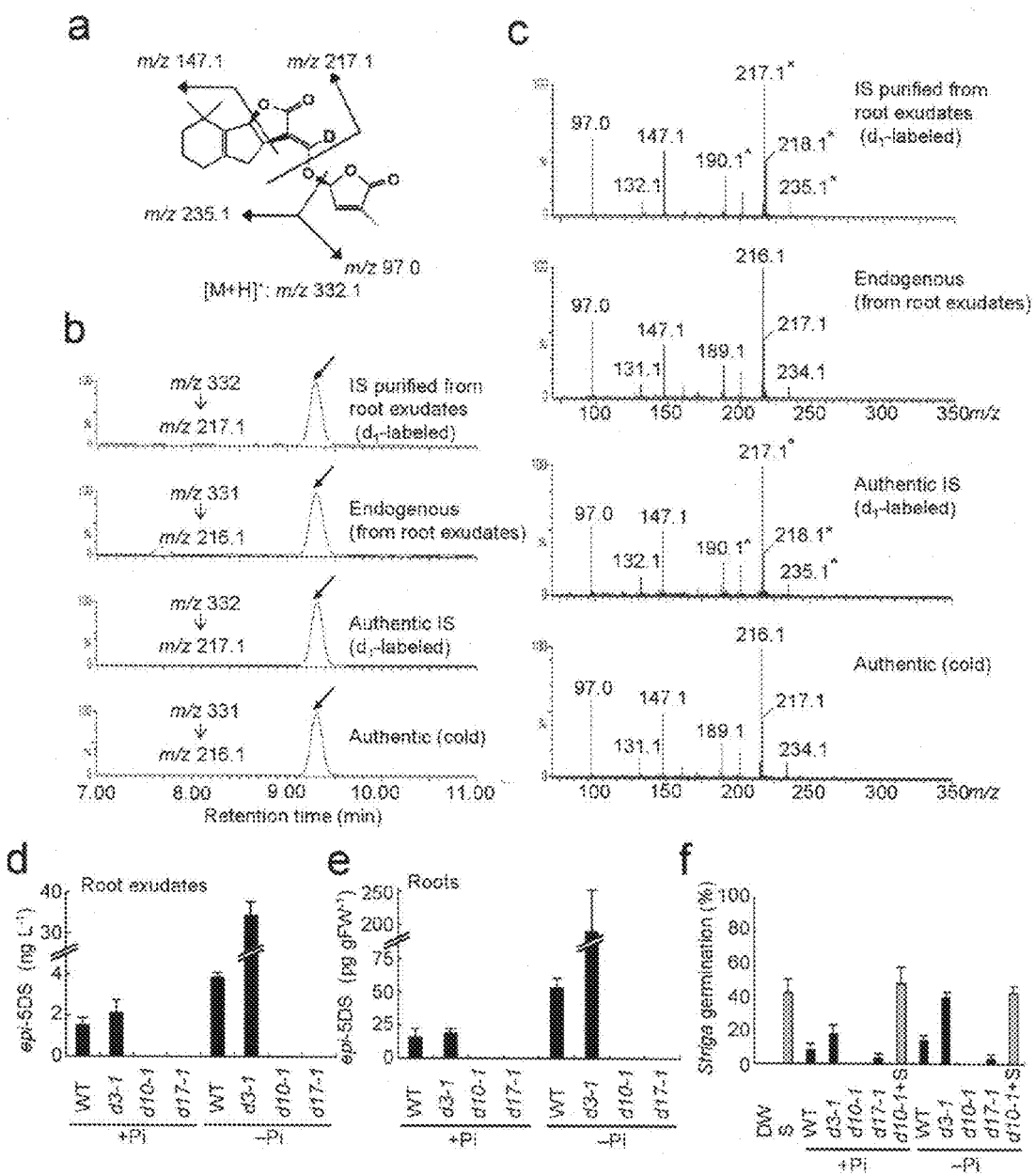
FIG. 2 shows strigolactone analysis in rice seedlings. a: Predicted major fragmentation patterns of $d_1$-epi-5DS on LC-MS/MS. b: Selected reaction monitoring for $d_1$-epi-5DS (internal standard, IS) or epi-5DS. c: Full-scan spectra of fragment ions. Asterisks, deuterium-labeled ions. d and e: LC-MS/MS analysis of epi-5DS levels in culture media (d) and in roots of wild type (WT) and d mutants (e) in the presence (+Pi) or absence (−Pi) of Pi (mean+s.d., n=3). f: Estimation of germination stimulant levels in culture media using *Striga* seeds (means+s.d., n=3). DW: distilled water; S: (+)-strigol ($10^{-7}$ M); d10-1+S: co-incubation with (+)-strigol ($10^{-7}$ M) and d10-1 culture media.
Figure 8:
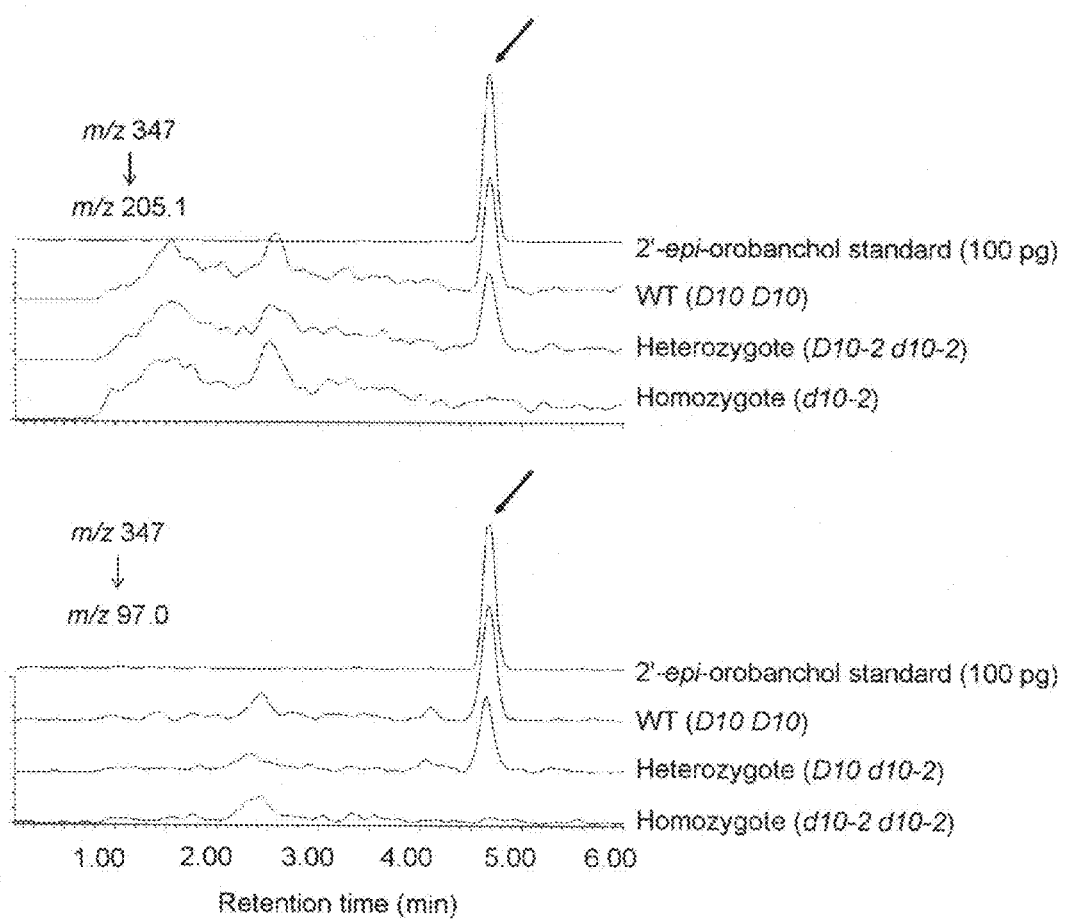
FIG. 8 shows LC-MS/MS analysis of strigolactones in root exudates of wild type and d10-2 mutant (Nipponbare background). Progenies of heterozygous D10 d10-2 plants were germinated and individual plants were genotyped by PCR using primers described in Table 1. Ten seedlings (2 weeks old) for each genotype were pooled and 2'-epi-orobanchol (or its isomer) in root exudates were analyzed by selected reaction monitoring on LC-MS/MS.

To explore the potential role of D10/CCD8 and D17/CCD7 in strigolactone biosynthesis in rice, we analyzed strigolactones in root exudates of wild type and d mutants (FIG. 6a) by liquid chromatography-quadrupole/time-of-flight tandem mass spectrometry (LC-MS/MS). Since our survey of known strigolactones in hydroponic culture media of rice seedlings (cv. Shiokari) identified 2'-epi-5-deoxystrigol (epi-5DS), we synthesized deuterium-labeled epi-5DS (FIG. 7) and used it as an internal standard for quantification on LC-MS/MS. We selected $[M+H]^+$ (m/z 332 and 331 for $d_1$- and cold epi-5DS, respectively) as parent ions on quadrupole MS and detected $[M+H-115]^+$ (m/z 217.1 and 216.1 for $d_1$- and cold epi-5DS, respectively) as fragment ions on time-of-flight MS after collision-induced dissociation (CID) for quantification (FIGS. 2a and 2b). Full-scan spectra of fragment ions confirmed the identity of these compounds (FIG. 2c). As observed for strigolactones in other species[28,30,31], the levels of epi-5DS in root exudates of wild type seedlings were elevated when phosphate (Pi) was depleted in the media (FIG. 2d). However, epi-5DS was nearly undetectable in exudates of d10-1 and d17-1 mutants, regardless of the nutrient conditions (FIG. 2d). Reduced levels of another strigolactone species (2'-epi-orobanchol or its isomer) in root exudates were also evident for the d10-2 allele in Nipponbare background (FIG. 8). To determine whether the production of epi-5DS was decreased or only the secretion from roots was defective in these mutants, we quantified endogenous epi-5DS in roots. We found that the endogenous levels of epi-5DS were also decreased in d10-1 and d17-1 seedlings relative to the wild type control (FIG. 2e). These results demonstrate that both D10/CCD8 and D17/CCD7 are required for the production of normal levels of strigolactones in rice seedlings.

In contrast to the d10-1 and d17-1 mutants, d3-1 seedlings accumulated higher levels of epi-5DS both in culture media and in roots than did wild type plants under Pi deficiency (FIGS. 2d and 2e). These results are correlated with the upregulation of D10/CCD8 transcript levels in d3-1 and other tillering d mutants[14], and further support the idea that D10/CCD8 participates in strigolactone biosynthesis. Similar transcriptional regulation of RMS1/CCD8 was also found in the rms4 mutant of pea, probably through a feedback inhibition mechanism in the branching inhibitor pathway[4]. The elevated strigolactone production in the d3 mutant suggest that the decreased strigolactone levels in the d10 and d17 mutants are attributed to a direct blockage of the biosynthesis pathway, rather than a secondary consequence of the decreased branching inhibitor activity, because in the latter case, strigolactone levels would be reduced also in the d3 mutant.

Pre-conditioned seeds of the parasitic plant *Striga hermonthica* require germination stimulants, including strigolactones, released from the host roots to complete germination. We employed a highly sensitive germination assay using *S. hermonthica* seeds to estimate strigolactone concentrations in root exudates of d mutants[27,32]. In agreement with the LC-MS/MS data, the culture media of d10-1 and d17-1 seedlings contained weaker germination-stimulating activity than did those of wild type plants (FIG. 2f). By contrast, d3-1 root exudates exhibited stronger germination-stimulating activity than the wild type control. The reduced germination-stimulating activity in d10-1 root exudates is not due to increased germination inhibitors, but to decreased germination stimulants, because the addition of d10-1 exudates did not inhibit germination induced by (+)-strigol (FIG. 2f). These results indicate that overall strigolactone levels released from roots are decreased in the d10-1 and d17-1 mutants.

Strigolactones Inhibit Tillering in Rice

Figure 3:
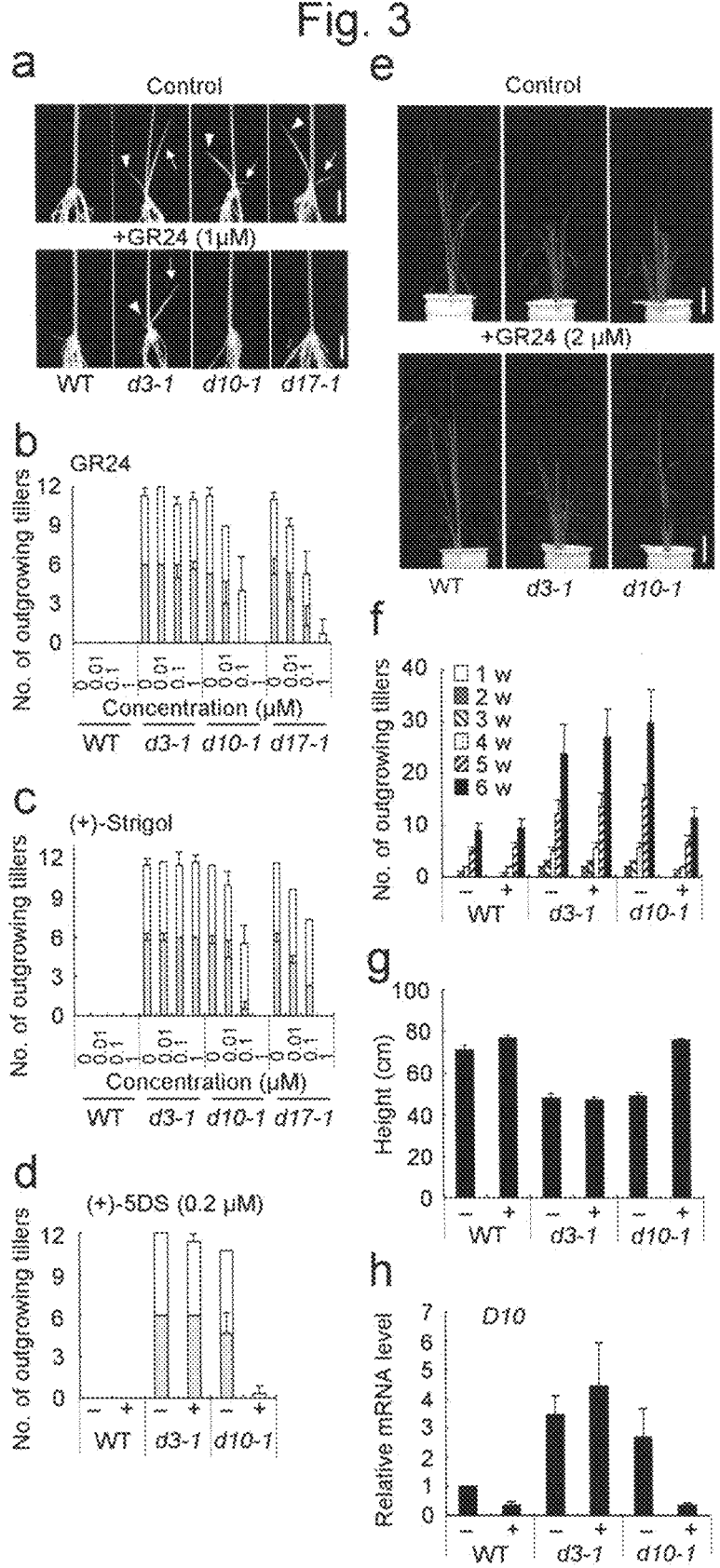
FIG. 3 shows inhibitory effect of strigolactones on tiller bud outgrowth of rice. a: Effect of 1 µM GR24 on wild type (WT) and d mutants. Arrow and arrowhead indicate the first and second tiller, respectively. Scale bar: 1 cm. b-d: The total number of tiller buds that grew over 2 mm in the absence or presence of GR24 (b), (+)-strigol (c) or (+)-5DS (d) in 6 seedlings (2 weeks old). Gray and white bars indicate the first and second tillers, respectively (mean+s.d., n=3). e-g: Six-week-old plants in the absence (−) or presence (+) of 2 µM GR24 in the culture media. (e) Scale bar: 10 cm. Weekly changes in the total number of tillers that grew over 2 mm (f) and the plant height at the 6th week (g) (mean+s.d., n=4). h: Relative D10 transcript levels in roots of 8-day-old seedlings after mock (−) or 1 µM (+)-GR24 treatment (+) for 24 h (mean+s.d., n=3).

To further investigate the relationships between the D10/D17-derived branching inhibitor and strigolactones, we examined the effect of strigolactone treatment on rice d mutants. We developed a hydroponic culture system using rice seedlings, where we observed outgrowth of first and second tiller (axillary) buds in the d mutants, but not in the wild type. An application of GR24 (a strigolactone analog; FIG. 1b) to the media inhibited tiller bud outgrowth of 2-week-old d10-1 and d17-1 seedlings in a dose-dependent manner (FIGS. 3a and 3b). The inhibitory effect was detectable in response to as low as 10 nM GR24, and tiller bud outgrowth was nearly fully inhibited at 1 µM GR24. In contrast to d10-1 and d17-1, the d3-1 mutant, defective in a probable signaling component (FIG. 1a), was insensitive to this chemical. No morphological abnormalities were evident in wild type seedlings after GR24 treatment. Similar effects were observed when we used naturally-occurring strigolactones, (+)-strigol and (+)-5DS, as well (FIGS. 1b, 3c and 3d). The insensitivity of the d3-1 mutant to strigolactones indicates that their inhibitory effects on tiller bud outgrowth were specific to the proposed branching inhibitor pathway. These results illustrate that strigolactones or downstream metabolites act as the novel branching inhibitor. The tillering dwarf phenotype of the d mutants is more drastic in appearance at later stage[12,33]. We found that the branching phenotype as well as the plant height of 6-week-old d10-1 mutant were complemented by including 2 µM GR24 in the culture media, while no visible effect of this chemical was recognizable in d3-1 mutant plants (FIGS. 3e-g). These results confirm the role of strigolactones in inhibiting tiller bud outgrowth in the branching inhibitor pathway in rice.

In many cases, hormonal responses are dose-dependent within a certain range and both hormone-deficiency and -excess phenotypes are observed. We next examined the effect of a high dose of GR24 on tillering of wild type seedlings. We found that tiller outgrowth was severely inhibited when 10 µM GR24 was supplemented to the culture media, without affecting the growth of main leaves (FIG. 9). These observations further support the role of strigolactones in inhibiting axillary bud outgrowth and suggest the potential usefulness of strigolactones as plant growth regulators that specifically inhibit branching.

As mentioned above, D10 transcript levels were previously shown to be elevated in the d3-1 and d10-1 mutants, suggesting a negative feedback control in the branch inhibitor pathway[14]. Our quantitative reverse transcription-PCR analysis revealed that GR24 treatment decreased D10 transcript levels in d10-1 and wild type seedlings, but not in the d3-1 mutant (FIG. 3h). These results, together with the elevated strigolactone production in the d3-1 mutant (FIG. 2), indicate that endogenous strigolactone levels are under homeostatic control via the D3-dependent signaling pathway and further support the idea that strigolactones (or downstream metabolites) act as the branching inhibitors in rice.

Strigolactones Inhibit Shoot Branching in Arabidopsis

Figure 4:
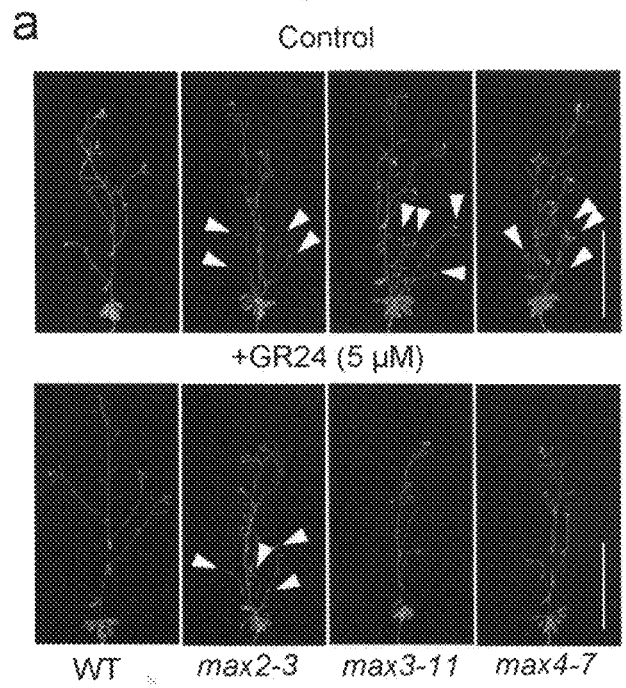
FIG. 4 shows inhibitory effect of GR24 on axillary bud outgrowth of *Arabidopsis*. a: Effect of 5 µM GR24 on 30-day-old wild type (WT) and max mutants. Arrowheads indicate outgrowth of axillary buds. Scale bar: 10 cm. b: Number of axillary shoots that grew over 5 mm (mean+s.d., n=12-16). c: Estimation of germination stimulant levels in culture media of 2-week-old seedlings using *S. hermonthica* seeds (mean+s.d., n=3). DW: distilled water; S: (+)-strigol ($10^{-7}$ M).
Figure 4:
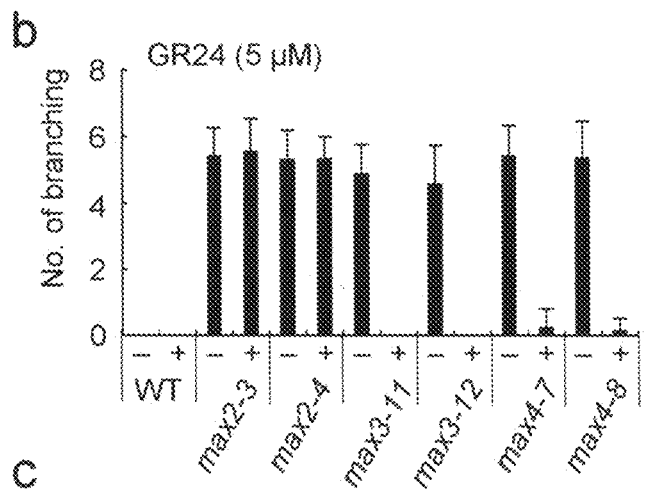
Figure 4:
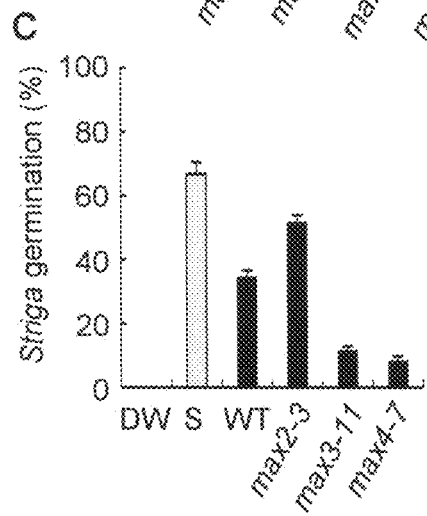

To determine whether strigolactones participate in the branching inhibitor pathway in Arabidopsis, we examined the effect of GR24 on the branching phenotype of max mutants (FIG. 6b). The MX genes are required for selective repression of axillary shoots and max mutants exhibit bushier shoots than do wild type plants[5,9]. Our data showed that the enhanced branching phenotype of max3 and max4 mutants (defective in CCD7 and CCD8, respectively; FIG. 1a) was rescued by supplementing 5 µM GR24 to the hydroponic culture media, whilst max2 mutants were insensitive to GR24 treatment (FIGS. 4a and 4b). Next, we estimated the levels of strigolactones in root exudates of max mutants by determining germination-stimulating activity using S. hermonthica seeds. In root exudates from max3 and max4 seedlings, the levels of germination stimulants were significantly lower than those from the wild type. By contrast, the max2 mutant exuded germination stimulants at slightly higher levels than did wild type (FIG. 4c). Collectively, these results suggest that strigolactones are biosynthesized from carotenoid cleavage products by CCD7 and CCD8 and inhibit shoot branching through the MAX-dependent pathway in Arabidopsis.

d10 Roots are Infected by Fewer Striga hermonthica Plants

We have identified strigolactone-deficient and -insensitive mutants. To explore the impact of altered strigolactone levels on the interaction with parasitic weeds, we utilized rice d mutants to observe germination, infection and the following developmental processes of S. hermonthica plants. S. hermonthica is an obligate root parasite and infests cereals[34,35], including rice (FIG. 5a). In the vicinity of d10-1 roots, fewer seeds germinated than did those co-incubated with wild type or d3-1 roots (FIG. 5b), consistent with the finding that d10-1 roots exude lower levels of strigolactones (FIGS. 2d and 2f). As a consequence of the reduced germination frequency, fewer S. hermonthica plants established parasitism with d10-1 in 2 weeks than with wild type or d3-1 (FIG. 5b). When S. hermonthica seeds were co-incubated with d10-1 seedlings after the induction of germination by (+)-strigol, there was no significant difference in the frequency of successful parasitism among the three genotypes (FIG. 5c). Albeit at a very low frequency, some S. hermonthica seeds germinated in the vicinity of d10-1 roots in the absence of (+)-strigol and then successfully infected. Together, these results indicate that fewer S. hermonthica plants can infect d10-1 roots principally due to lower levels of germination stimulants released from this host. Our results also suggest that, once the S. hermonthica seeds germinate, strigolactone-deficiency does not significantly affect the following infection processes. We cannot rule out the possibility that a small amount of strigolactones due to residual CCD8 activity might exist in the d10-1 mutant and affect the germination and infection of S. hermonthica, because the d10-1 mutation results in a single amino acid substitution (FIG. 6) and may not be a null allele.

Discussion

Outgrowth of axillary buds is in part regulated by the interaction of multiple hormonal signals[15]; auxin is actively transported downwards in the shoots and inhibits bud outgrowth, whereas cytokinins move upwards in plants and activate bud outgrowth. We have shown that the d and max branching mutants of rice and Arabidopsis are deficient in or insensitive to strigolactones, and that exogenously applied strigolactones inhibit shoot branching. Thus, we propose that strigolactones or downstream metabolites act as the long searched new hormones in the D/MAX pathway. It should be noted, however, that the bioactive form(s) of this new class of hormones has not been clarified in the current study. Extensive survey of natural strigolactones as seed germination stimulants of root parasites and hyphal branching inducers of AM fungi revealed highly diverse structures, attributable to modifications on ring ABC and the C2'-configuration[29,36] (FIG. 1b). Moreover, it has been unknown how these diverse strigolactones are further metabolized in plants. Elucidation of the bioactive form(s) of the branch-inhibiting hormones is a critical next question in order to explore the distribution, movement and perception of this chemical signal in plants. Shoot branching is influenced by a wide range of environmental signals[37]. Our findings suggest that strigolactones may play a key role in mediating the detection of nutrient availability by roots and the resulting alterations in shoot architecture, provided that strigolactone levels were increased in response to Pi-deficiency, particularly in hosts of AM fungi[26,28,30,31] (FIGS. 2d-f); upon Pi (and possibly other nutrients) starvation, a probable adoptive strategy of plants would be to synthesize strigolactones for minimizing shoot branching and maximizing the symbiotic interaction with AM fungi that facilitate the uptake of mineral nutrients. Root parasitic weed seeds abuse these chemical signals secreted for the successful symbiosis with AM fungi to find their potential hosts in soil.

Figure 5:
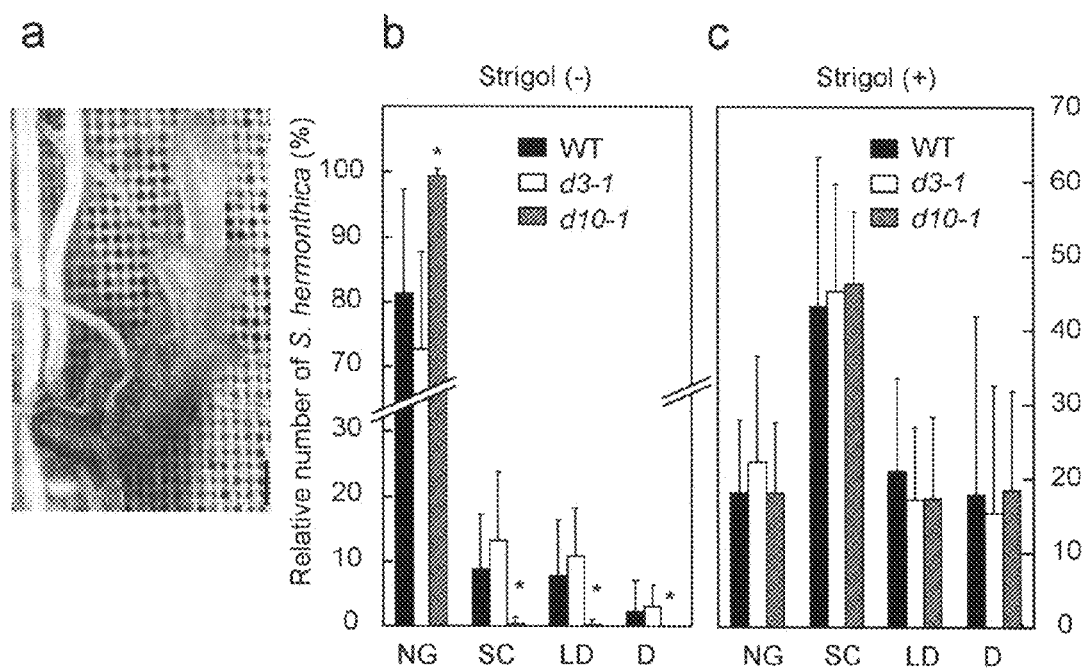
FIG. 5 shows infection of rice d mutants by *Striga hermonthica*. a: *Striga* parasitizing to rice roots 4 weeks after inoculation. Scale bar: 500 µm. b and c: Infection of *Striga* on wild type (WT; black), d3-1 (white) and d10-1 (stripe) roots 2 weeks after the inoculation of *Striga* seeds treated with (c) or without (b) (+)-strigol. Shown are the ratio of number of *Striga* plants at each developmental stage to the total number of co-incubated *Striga* seeds (mean+s.d., b: n=16-17; c: n=23-24). NG: no germination; SC: penetration succeeded and seed coat remained attached; LD: leaf developed after the establishment of parasitism; D: died after penetration. Asterisks: significantly different from wild type (Student's t-test, P<0.05).

In many parts of the world, the parasitic weeds *Striga* and *Orobanche* are serious agricultural pests[34,35]. Strigolactones have been an important target for parasitic weed control in generating low-germination stimulant varieties 21. Although strigolactones have been chemically recognized for decades, the biosynthetic pathway had not been genetically defined. The identification of several D/MAX loci as strigolactone biosynthesis genes now allows us to take a first step towards designing new varieties with reduced risk of parasite infections in molecular breeding. In fact, our results showed that, at least in an experimental condition, the rice d10-1 mutant was infected by significantly fewer *S. hermonthica* plants in comparison with wild type, as a consequence of decreased germination frequency of the parasite seeds near the host root (FIG. 5). The use of strigolactone-deficient mutant will also facilitate our understanding on the exact roles of this class of terpenes in communication with AM fungi in the rhizosphere.

References
1. Beveridge, C. A., Ross, J. J. & Murfet, I. C. Branching mutant rms-2 in *Pisum sativum*. Grafting studies and endogenous indole-3-acetic acid levels. *Plant Physiol.* 104, 953-959 (1994).
2. Beveridge, C. A., Ross, J. J. & Murfet, I. C. Branching in Pea (Action of Genes Rms3 and Rms4). *Plant Physiol.* 110, 859-865 (1996).
3. Beveridge, C. A., Symons, G. M. & Turnbull, C. G. Auxin inhibition of decapitation-induced branching is dependent on graft-transmissible signals regulated by genes Rms1 and Rms2. *Plant Physiol.* 123, 689-697 (2000).
4. Johnson, X. et al. Branching genes are conserved across species. Genes controlling a novel signal in pea are correlated by other long-distance signals. *Plant Physiol.* 142, 1014-1026 (2006).
5. Stirnberg, P., van De Sande, K. & Leyser, O. MAX1 and MAX2 control shoot lateral branching in *Arabidopsis*. *Development* 129, 1131-1141 (2002).
6. Sorefan, K. et al. MAX4 and RMS1 are orthologous dioxygenase-like genes that regulate shoot branching in *Arabidopsis* and pea. *Genes Dev.* 17, 1469-1474 (2003).
7. Booker, J. et al. MAX3/CCD7 is a carotenoid cleavage dioxygenase required for the synthesis of a novel plant signaling molecule. *Curr Biol.* 14, 1232-1238 (2004).
8. Booker, J. et al. MAX1 encodes a cytochrome P450 family member that acts downstream of MAX3/4 to produce a carotenoid-derived branch-inhibiting hormone. *Dev. Cell* 8, 443-449 (2005).
9. Turnbull, C. G, Booker, J. P. & Leyser, O. Micrografting techniques for testing long-distance signalling in *Arabidopsis*. *Plant J.* 32, 255-262 (2002).
10. Snowden, K. C. et al. The Decreased apical dominance1/*Petunia hybrida* CAROTENOID CLEAVAGE DIOXYGENASE8 gene affects branch production and plays a role in leaf senescence, root growth, and flower development. *Plant Cell* 17, 746-759 (2005).
11. Simons, J. L., Napoli, C. A., Janssen, B. J., Plummer, K. M. & Snowden, K. C. Analysis of the DECREASED APICAL DOMINANCE genes of petunia in the control of axillary branching. *Plant Physiol.* 143, 697-706 (2007).
12. Ishikawa, S. et al. Suppression of tiller bud activity in tillering dwarf mutants of rice. *Plant Cell Physiol.* 46, 79-86 (2005).
13. Zou, J. et al. The rice HIGH-TILLERING DWARF1 encoding an ortholog of *Arabidopsis* MAX3 is required for negative regulation of the outgrowth of axillary buds. *Plant J.* 48, 687-698 (2006).
14. Arite, T. et al. DWARF10, an RMS1/MAX4/DAD1 ortholog, controls lateral bud outgrowth in rice. *Plant J.* 51, 1019-1029 (2007).
15. Ongaro, V & Leyser, O. Hormonal control of shoot branching. *J. Exp. Bot.* 59, 67-74 (2008).
16. Schwartz, S. H., Qin, X. & Loewen, M. C. The biochemical characterization of two carotenoid cleavage enzymes from *Arabidopsis* indicates that a carotenoid-derived compound inhibits lateral branching. *J. Biol. Chem.* 279, 46940-46945 (2004).
17. Auldridge, M. E. et al. Characterization of three members of the *Arabidopsis* carotenoid cleavage dioxygenase family demonstrates the divergent roles of this multifunctional enzyme family. *Plant J.* 45, 982-993 (2006).
18. Lechner, E., Achard, P., Vansiri, A., Potuschak, T. & Genschik, P. F-box proteins everywhere. *Curr Opin. Plant Biol.* 9, 631-638 (2006).
19. Cook, C. E. et al. Germination stimulants II. The structure of strigol-a potent seed germination stimulant for witchweed (*Striga lutea* Lour.). *J. Am. Chem. Soc.* 94, 6198-6199 (1972).
20. Humphrey, A. J. & Beale, M. H. Strigol: Biogenesis and physiological activity. *Phytochemistry* 67, 636-640 (2006).
21. Bouwmeester, H. J., Matusova, R., Zhongkui, S. & Beale, M. H. Secondary metabolite signalling in host-parasitic plant interactions. *Curr Opin. Plant Biol.* 6, 358-364 (2003).
22. Akiyama, K., Matsuzaki, K. & Hayashi, H. Plant sesquiterpenes induce hyphal branching in arbuscular mycorrhizal fungi. *Nature* 435, 824-827 (2005).
23. Bradow, J. M., Connick Jr, W. J., Pepperman, A. B. & Wartelle, L. H. Germination stimulation in wild oats (*Avena fatua* L.) by synthetic strigol analogues and gibberellic acid. *J. Plant Growth Regul.* 9, 35-41 (1990).
24. Bradow, J. M., Connick, W. J. & Pepperman, A. B. Comparison of the seed germination effects of synthetic analogs of strigol, gibberellic acid, cytokinins and other plant growth regulators. *J. Plant Growth Regul.* 7, 227-239 (1988).
25. Goldwasser, Y., Yoneyama, K., Xie, X. & Yoneyama, K. Production of strigolactones by *Arabidopsis thaliana* responsible for *Orobanche aegyptiaca* seed germination. *Plant Growth Regul.* 55, 21-28 (2008).
26. Yoneyama, K. et al. Strigolactones, host recognition signals for root parasitic plants and arbuscular mycorrhizal fungi, from Fabaceae plants. *New Phytol.* 179, 484-494. (2008).
27. Matusova, R. et al. The strigolactone germination stimulants of the plant-parasitic *Striga* and *Orobanche* spp. are derived from the carotenoid pathway. *Plant Physiol.* 139, 920-934 (2005).

28. López-Ráez, J. A. et al. Tomato strigolactones are derived from carotenoids and their biosynthesis is promoted by phosphate starvation. *New Phytol.* 178, 863-874. (2008).
29. Bouwmeester, H. J., Roux, C., Lopez-Raez, J. A. & Bécard, G Rhizosphere communication of plants, parasitic plants and AM fungi. *Trends Plant Sci.* 12, 224-230 (2007).
30. Yoneyama, K. et al. Nitrogen deficiency as well as phosphorus deficiency in sorghum promotes the production and exudation of 5-deoxystrigol, the host recognition signal for arbuscular mycorrhizal fungi and root parasites. *Planta* 227, 125-132 (2007).
31. Yoneyama, K., Yoneyama, K., Takeuchi, Y. & Sekimoto, H. Phosphorus deficiency in red clover promotes exudation of orobanchol, the signal for mycorrhizal symbionts and germination stimulant for root parasites. *Planta* 225, 1031-1038 (2007).
32. Sugimoto, Y. & Ueyama, T. Production of (+)-5-deoxystrigol by *Lotus japonicus* root culture. *Phytochemistry* 69, 212-217 (2008).
33. Zou, J. et al. Characterizations and fine mapping of a mutant gene for high tillering and dwarf in rice (*Oryza sativa* L.). *Planta* 222, 604-612 (2005).
34. Gressel, J. et al. Major heretofore intractable biotic constraints to Africa food security that may be amenable to novel biotechnological solutions. *Crop Prot.* 23, 661-689 (2004).
35. Joel, D. M. The long-term approach to parasitic weeds control: manipulation of specific developmental mechanisms of the parasite. *Crop Prot.* 19, 753-758 (2000).
36. Xie, X., Kusumoto, D., Takeuchi, Y, Yoneyama, K., Yamada, Y. & Yoneyama, K. 2'-Epi-orobanchol and solanacol, two unique strigolactones, germination stimulants for root parasitic weeds, produced by tobacco. *J. Agric. Food Chem.* 55, 8067-8072 (2007).
37. Cline, M. G Apical dominance. *The Botanical Review* 57, 318-358. (1991).
38. Magome, H., Yamaguchi, S., Hanada, A., Kamiya, Y. & Oda, K. dwarf and delayed-flowering 1, a novel *Arabidopsis* mutant deficient in gibberellin biosynthesis because of overexpression of a putative AP2 transcription factor. *Plant J.* 37, 720-729 (2004).
39. Kamachi, K., Yamane, T., Mae, T. & Ojima, K. A role for glutamine synthetase in the recombination of leaf nitrogen during natural senescence in rice leaves. *Plant Physiol.* 96, 411-417 (1991).
40. Murashige, T. & Skoog, F. A revised medium for rapid growth and bioassays with tobacco tissue cultures. *Physiol. Plant.* 15, 473-497 (1962).
41. Norén, H., Svensson, P. & Andersson, B. A convenient and versatile hydroponic cultivation system for *Arabidopsis thaliana*. *Physiol. Plant.* 121, 343-348 (2004)
42. Varbanova, M. et al. Methylation of gibberellins by *Arabidopsis* GAMT1 and GAMT2. *Plant Cell* 19, 32-45 (2007)
43. Mangnus, E. M., Jan Dommerholt, F., de Jong, R. L. P. & Zwaneburg, B. Improved synthesis of strigol analogue GR24 and evaluation of the biological activity of its diastereomers. *J. Agric. Food Chem.* 40, 1230-1235 (1992)
44. Gurney, A. L., Slate, J., Press, C. & Scholes, J. D. A novel form of resistance in rice to the angiosperm parasite *Striga hermonthica*. *New Phytol.* 169, 199-208 (2006)

Industrial Applicability

The present invention can effectively protect plants such as agricultural crops from root parasitic plants. Since the present invention can effectively protect plants from root parasitic plants, agricultural crops can be produced at a low cost in the agricultural field.

All publications, patents, and patent applications cited herein are incorporated herein by reference in their entirety.

The invention claimed is:

1. A method for protecting plants from root parasitic plants comprising decreasing the activity of a CCD7 or CCD8 carotenoid cleavage dioxygenase in the plants or the expression of a CCD7 or CCD8 gene encoding the carotenoid cleavage dioxygenase in the plants, by introducing into the plants a mutataion in said CCD7 or CCD8 gene or by inhibiting translation of mRNA of CCD7 or CCD8 in the plant, thereby decreasing the amount of strigolactone synthesized by the plants.

2. The method according to claim 1, wherein the gene encoding a carotenoid cleavage dioxygenase is any of the following genes (a) to (c):

(a) a gene selected from the group of genes consisting of nucleotide sequences as shown in SEQ ID NOs: 1, 3, 5, and 7;

(b) a gene consisting of a nucleotide sequence derived from the nucleotide sequence described in (a) by deletion, substitution, and/or addition of 1 or several nucleotides and encoding a protein having carotenoid cleavage dioxygenase activity; and (c) a gene hybridizing under stringent conditions to DNA complementary to the nucleotide sequence described in (a) and encoding a protein having carotenoid cleavage dioxygenase activity,

* * * * *

SEQUENCE LISTING

<160> NUMBER OF SEQ ID NOS: 30

<210> SEQ ID NO 1
<211> LENGTH: 2626
<212> TYPE: DNA
<213> ORGANISM: Oryza sativa

<400> SEQUENCE: 1

```
aacgaccgaa ggaggccaag tccaaagatg gcaacacaag cgattgcacc gatgcacgcc      60
gccgtcgtgc accgccacca cgttctacca ccccgccgct gcgtgcgccg ccgtggcgtc     120
ttcgtccgcg cctcggccgc cgccgccgcc gccgccgccg agacggacac gctgtccgcg     180
gccttctggg actacaacct cctcttccgg tgcagcgcg acgagtgcct cgactccatc      240
ccgctccgcg tcaccgaggg cgcgatcccg cccgacttcc cggccggcac ctactacctc     300
gccgggccgg gcatcttctc cgacgaccac ggctccaccg tccaccccct cgacggccac     360
ggctacctcc gtccttccg cttccggccc ggcgaccgca ccatccacta ctccgcgcgg     420
taagtcgcgc cgcgcgcatg cagcagcagc aggtttgtca gtgagagcga cagactgaca     480
gtgcacgcgt gagtgacgca tgcaggttcg tggacggc ggcgaagagg gaggagagcc       540
gggacggcgc gtcgtggcgg ttcacgcacc gggggcccttt ctccgtgctg cagggcggga    600
agaaggtggg caatgtgaag gtgatgaaga acgtggccaa caccagcgtg ctgcggtggg     660
gcggccggct gctctgcctc tgggagggcg gccagccgta cgaggttgac ccccggacgc     720
tcgagaccgt cggcccgttc gacctgctcg gcctcgccgc cgccgacgac aacaaggcaa     780
```

-continued

```
cgaacgcgtc tgcagcacga cggccgtggc tgcaggaggc cggcctcgac gccgccgcgc    840
gcctgctgcg ccctgttctt agcggtgcgt gacactgtac cggagcagcg gcctccactt    900
cgatcgattc ggaccgaact gatatgacgc tggtgcgcgc gtgcgtgcgt gcggtgcagg    960
ggtgttcgac atgccgggca agaggctgct ggcgcactac aagatcgacc gcggcggggg   1020
gcgtctgctg atggtcgcct gcaacgccga ggacatgctc ctcccgcgat cccacttcac   1080
tttctacggt cagctcgcca tcgcctcgac caaccacgca ttttccattc gctcctccaa   1140
aaaaaaaaat cacattgaac ggcgtttcca tggcagagtt cgacgcccac ttcgacctcg   1200
tccagaagcg tgagttcgtc gtgccggacc acctcatgat ccacgactgg gccttcaccg   1260
acacccacta catcctcctc ggcaacagga tcaagctcga catccccggt aaggaagaga   1320
aaacaaaaga aaacttgtcc atggaatgat ggaatcgtgc gcgcactggc gtctgatgct   1380
gacgtttggt atgcttggtt ggtgccgtgt tcgggcgtag gatcgctgct ggcattgacg   1440
ggcactcacc cgatgatcgc ggcgctggcc gtggacccga aaggcagtc gacgccggtg   1500 tacctgcttc cgcgctcccc ggagaccgag gcgggcggcc gcgactggag cgtgccgatc   1560
gaggcgccgt cgcagatgtg gtccgtgcac gtcggcaacg cgttcgagga ggcgaaccgc   1620
cggggcggcc tcgacgtccg gctgcacatg tcaagctgct cctaccagtg gttccatttc   1680
cacaggatgt ttggtaaatt tcaacgccac aaaaaaaaaa acagtaatcc atatttgctc   1740
gttcttgcat ttgcacattg ctggaacaca acgatcatcg agtgatctgc atcacaggtt   1800
acaattggca ccacaagaag ctggacccgt cgttcatgaa cgcggcgaag ggaaaggagt   1860
ggctgcctcg cctcgttcag gtggccatcg agctcgacag gacgggagag tgccggaggt   1920
gctcagtcag gaggctgtcc gatcagcacg ccaggccggc ggacttcccg gcgataaacc   1980
caagctacgc caaccagagg aaccggttcg tctacgccgg cgccgcgtcc ggctcccgca   2040
gattcctccc gtacttcccg ttcgacagcg tggtgaaggt cgacgtctcc gatggatcgg   2100
cgcggtggtg gtctaccgac gggcgcaagt cgtcggcga ccggtcttc gtcccgaccg   2160 gcggcggaga ggatggtggc tatgttcttc ttgtagaggt aagacggagt gcccgttcca   2220
tcaacatgaa gtacgagtgt tttgtttttt cttaagattt agtacaaatg tttactactg   2280
aattaacatc aagacatgtg atgtctcttt gcttcttgac agtatgcagt ctccaagcac   2340
agatgccatc tagtggtgct ggatgcaaag aagatagga cagagaatgc acttgtggca   2400
aaactagagg tgccaaagaa cctcactttt ccaatgggat tccatggttt ctggggagat   2460
gaatgagcat agagcaagca tcagatccag tctaactctg gagagaaatt gtcttgaaaa   2520
ggcaagaatt ttgcctcgtg tattgataaa agagagtttt gtgataatct gtacatggtg   2580
gagaggaatt atcaggggaa ccaaataact actgtacatc cagtct               2626
```

<210> SEQ ID NO 2
<211> LENGTH: 609
<212> TYPE: PRT
<213> ORGANISM: Oryza sativa

<400> SEQUENCE: 2

```
Met Ala Thr Gln Ala Ile Ala Pro Met His Ala Val Val His Arg
1               5                  10                  15

His His Val Leu Pro Pro Arg Arg Cys Val Arg Arg Gly Val Phe
                20                  25                  30

Val Arg Ala Ser Ala Ala Ala Ala Ala Ala Ala Glu Thr Asp Thr
            35                  40                  45
```

```
Leu Ser Ala Ala Phe Trp Asp Tyr Asn Leu Leu Phe Arg Ser Gln Arg
         50                  55                  60

Asp Glu Cys Leu Asp Ser Ile Pro Leu Arg Val Thr Glu Gly Ala Ile
 65                  70                  75                  80

Pro Pro Asp Phe Pro Ala Gly Thr Tyr Tyr Leu Ala Gly Pro Gly Ile
                 85                  90                  95

Phe Ser Asp Asp His Gly Ser Thr Val His Pro Leu Asp Gly His Gly
            100                 105                 110

Tyr Leu Arg Ser Phe Arg Phe Arg Pro Gly Asp Arg Thr Ile His Tyr
        115                 120                 125

Ser Ala Arg Phe Val Glu Thr Ala Ala Lys Arg Glu Glu Ser Arg Asp
    130                 135                 140

Gly Ala Ser Trp Arg Phe Thr His Arg Gly Pro Phe Ser Val Leu Gln
145                 150                 155                 160

Gly Gly Lys Lys Val Gly Asn Val Lys Val Met Lys Asn Val Ala Asn
                165                 170                 175

Thr Ser Val Leu Arg Trp Gly Gly Arg Leu Leu Cys Leu Trp Glu Gly
            180                 185                 190

Gly Gln Pro Tyr Glu Val Asp Pro Arg Thr Leu Glu Thr Val Gly Pro
        195                 200                 205

Phe Asp Leu Leu Gly Leu Ala Ala Ala Asp Asp Asn Lys Ala Thr Asn
    210                 215                 220

Ala Ser Ala Ala Arg Arg Pro Trp Leu Gln Glu Ala Gly Leu Asp Ala
225                 230                 235                 240

Ala Ala Arg Leu Leu Arg Pro Val Leu Ser Gly Val Phe Asp Met Pro
                245                 250                 255

Gly Lys Arg Leu Leu Ala His Tyr Lys Ile Asp Pro Arg Arg Gly Arg
            260                 265                 270

Leu Leu Met Val Ala Cys Asn Ala Glu Asp Met Leu Leu Pro Arg Ser
        275                 280                 285

His Phe Thr Phe Tyr Glu Phe Asp Ala His Phe Asp Leu Val Gln Lys
    290                 295                 300

Arg Glu Phe Val Val Pro Asp His Leu Met Ile His Asp Trp Ala Phe
305                 310                 315                 320

Thr Asp Thr His Tyr Ile Leu Leu Gly Asn Arg Ile Lys Leu Asp Ile
                325                 330                 335

Pro Gly Ser Leu Leu Ala Leu Thr Gly Thr His Pro Met Ile Ala Ala
            340                 345                 350

Leu Ala Val Asp Pro Arg Arg Gln Ser Thr Pro Val Tyr Leu Leu Pro
        355                 360                 365

Arg Ser Pro Glu Thr Glu Ala Gly Gly Arg Asp Trp Ser Val Pro Ile
    370                 375                 380

Glu Ala Pro Ser Gln Met Trp Ser Val His Val Gly Asn Ala Phe Glu
385                 390                 395                 400

Glu Ala Asn Arg Arg Gly Gly Leu Asp Val Arg Leu His Met Ser Ser
                405                 410                 415

Cys Ser Tyr Gln Trp Phe His Phe His Arg Met Phe Gly Tyr Asn Trp
            420                 425                 430

His His Lys Lys Leu Asp Pro Ser Phe Met Asn Ala Ala Lys Gly Lys
        435                 440                 445

Glu Trp Leu Pro Arg Leu Val Gln Val Ala Ile Glu Leu Asp Arg Thr
    450                 455                 460

Gly Glu Cys Arg Arg Cys Ser Val Arg Arg Leu Ser Asp Gln His Ala
465                 470                 475                 480
```

-continued

```
Arg Pro Ala Asp Phe Pro Ala Ile Asn Pro Ser Tyr Ala Asn Gln Arg
                485                 490                 495

Asn Arg Phe Val Tyr Ala Gly Ala Ala Ser Gly Ser Arg Arg Phe Leu
            500                 505                 510

Pro Tyr Phe Pro Phe Asp Ser Val Val Lys Val Asp Val Ser Asp Gly
        515                 520                 525

Ser Ala Arg Trp Trp Ser Thr Asp Gly Arg Lys Phe Val Gly Glu Pro
    530                 535                 540

Val Phe Val Pro Thr Gly Gly Glu Asp Gly Gly Tyr Val Leu Leu
545                 550                 555                 560

Val Glu Tyr Ala Val Ser Lys His Arg Cys His Leu Val Leu Asp
                565                 570                 575

Ala Lys Lys Ile Gly Thr Glu Asn Ala Leu Val Ala Lys Leu Glu Val
            580                 585                 590

Pro Lys Asn Leu Thr Phe Pro Met Gly Phe His Gly Phe Trp Gly Asp
        595                 600                 605

Glu
```

<210> SEQ ID NO 3
<211> LENGTH: 2396
<212> TYPE: DNA
<213> ORGANISM: Arabidopsis thaliana

<400> SEQUENCE: 3

```
atgtctctcc ctatcccgcc gaaatttctt ccaccgctaa aatctccacc gattcatcat    60
caccaaactc cgccaccgct tgcacctcca cgagccgcaa atcaatatc tataccagac   120
accggtttag gacgtaccgg taccatcctc gacgagtcca cgtcttcagc tttccgtgat   180
taccaatctt tattcgtgtc acaacgttcc gagactatcg aaccggtcgt aattaaacca   240
atcgaaggtt caataccggt taacttccct tccggtacat actacttagc cggtccagga   300
ctatttactg acgaccatgg ctcaacggtt catcctttag acggtcacgg ttatctccgt   360
gcgtttcaca tcgacggtaa caaacggaaa gccactttca cggcgaagta cgttaaaacg   420
gaagctaaaa aagaagagca cgatcctgta actgacacgt ggcggttcac tcatagaggt   480
cctttctcgg tgttgaaagg agggaagaga tttggaaaca cgaaagtgat gaaaaacgtg   540
gctaatacta gcgttttgaa atgggctggg cgattgcttt gtttatggga aggtggtgaa   600
ccgtacgaga ttgaatctgg atcgttggat accgtcggaa gatttaacgt cgagaacaac   660
ggttgtgaat cttgtgatga tgatgattct tccgacagag atttatctgg tcatgatata   720
tgggacacag ccgcagattt gttgaaaccc atacttcaag gtaatgttta tgttaaagta   780
gtaaagttaa ataacttaa agtatgtagt cctttattca gacagcggcg taaaattaat   840
taatgcaaca aaactatata gtaaaacttt ttattcaaat atgtaggtgt atttaagatg   900
ccaccgaaac ggttcttgtc acattacaaa gtcgacggtc gaagaaaaag acttttaacg   960
gtcacttgca acgctgaaga tatgctttta cctcgaagca acttcacatt ttgtggtaaa  1020
taatcttta attctttaaa aacattatga aaatagtat ttattattat tgtagttgta  1080
atggcaatta actatttaca gagtatgatt cggaattcaa gttgatacaa acgaaagaat  1140
tcaagatcga tgatcatatg atgattcatg attgggcatt cacggatact cactacatac  1200
tctttgccaa ccgagtcaag cttaatccaa taggtaaagt tatcttgata gtaataagtt  1260
ctgtttcaag tcatttacgt acacgaagaa taatacttgc gttacaagaa atctgatgat  1320
gtaaaatata cacacgcagg ttccatagcg gctatgtgcg gaatgtcacc aatggtatca  1380
```

-continued

```
gcgttatcgt taaacccaag caacgagagt tctccgattt atattctccc taggttttct    1440
gataaatatt ctaggggagg tcgagactgg agagttcctg tcgaagtgtc ttctcaatta    1500
tggctaatac actccggaaa cgcttatgag actagagagg ataacggcga tttaaagatt    1560
cagatacaag cttccgcttg ttcttaccga tggttcgatt tccagaaaat gtttggtaag    1620
ttaagaagtc accaaataca aacctatata agactatttc gaaataaccct ctttcacaag    1680 ttagggcttt tagggtgttc aaacgacagc tattgaacat tttttcaaaa aaattcttat    1740
aggctatgat tggcaaagca acaagctgga tccttctgtt atgaatctaa accgtggcga    1800
cgacaaacta ctccctcatc tagttaaggt gtctatgact ttggactcta ccggaaactg    1860
caatagttgt gatgtagagc ctctaaacgg gtggaacaag ccgtcagatt ttccggttat    1920
aaactcatcc tggtccggaa aaagaacaa gtacatgtac tctgctgcct cgtcgggaac    1980
tcgaagtgaa cttccccatt ttccattcga catggtcgtg aaatttgact tagactcaaa    2040
cctcgtccgt acttggtcta ccggagctag aagattcgtt ggtgagccca tgtttgtccc    2100
aaaaaactct gttgaagaag gagaagaaga ggacgatggt tacattgtcg tggtcgaggt    2160
acgtatatat atcaacactt tcgttttttc tcttttagat atgcatgttg tgcgtatatt    2220
tgatacaaat ttgtcatttg ctatttttat agtatgcggt ttcggtggag agatgttacc    2280 tagtgattt ggatgctaag aagatcggtg aatccgatgc ggtcgtgtcg aggttagagg    2340
ttccgaggaa tttgacgttt ccgatgggtt ttcatggttt atgggctagc gactga       2396
```

<210> SEQ ID NO 4
<211> LENGTH: 618
<212> TYPE: PRT
<213> ORGANISM: Arabidopsis thaliana

<400> SEQUENCE: 4

```
Met Ser Leu Pro Ile Pro Pro Lys Phe Leu Pro Pro Leu Ser Pro
1               5                   10                  15

Pro Ile His His His Gln Thr Pro Pro Leu Ala Pro Pro Arg Ala
                20                  25                  30

Ala Ile Ser Ile Ser Ile Pro Asp Thr Gly Leu Gly Arg Thr Gly Thr
            35                  40                  45

Ile Leu Asp Glu Ser Thr Ser Ser Ala Phe Arg Asp Tyr Gln Ser Leu
        50                  55                  60

Phe Val Ser Gln Arg Ser Glu Thr Ile Glu Pro Val Val Ile Lys Pro
65                  70                  75                  80

Ile Glu Gly Ser Ile Pro Val Asn Phe Pro Ser Gly Thr Tyr Tyr Leu
                85                  90                  95

Ala Gly Pro Gly Leu Phe Thr Asp Asp His Gly Ser Thr Val His Pro
            100                 105                 110

Leu Asp Gly His Gly Tyr Leu Arg Ala Phe His Ile Asp Gly Asn Lys
        115                 120                 125

Arg Lys Ala Thr Phe Thr Ala Lys Tyr Val Lys Thr Glu Ala Lys Lys
    130                 135                 140

Glu Glu His Asp Pro Val Thr Asp Thr Trp Arg Phe Thr His Arg Gly
145                 150                 155                 160

Pro Phe Ser Val Leu Lys Gly Gly Lys Arg Phe Gly Asn Thr Lys Val
                165                 170                 175

Met Lys Asn Val Ala Asn Thr Ser Val Leu Lys Trp Ala Gly Arg Leu
            180                 185                 190

Leu Cys Leu Trp Glu Gly Gly Glu Pro Tyr Glu Ile Glu Ser Gly Ser
        195                 200                 205
```

```
Leu Asp Thr Val Gly Arg Phe Asn Val Glu Asn Asn Gly Cys Glu Ser
210                 215                 220
Cys Asp Asp Asp Asp Ser Ser Asp Arg Asp Leu Ser Gly His Asp Ile
225                 230                 235                 240
Trp Asp Thr Ala Ala Asp Leu Leu Lys Pro Ile Leu Gln Gly Val Phe
                245                 250                 255
Lys Met Pro Pro Lys Arg Phe Leu Ser His Tyr Lys Val Asp Gly Arg
            260                 265                 270
Arg Lys Arg Leu Leu Thr Val Thr Cys Asn Ala Glu Asp Met Leu Leu
        275                 280                 285
Pro Arg Ser Asn Phe Thr Phe Cys Glu Tyr Asp Ser Glu Phe Lys Leu
    290                 295                 300
Ile Gln Thr Lys Glu Phe Lys Ile Asp Asp His Met Met Ile His Asp
305                 310                 315                 320
Trp Ala Phe Thr Asp Thr His Tyr Ile Leu Phe Ala Asn Arg Val Lys
                325                 330                 335
Leu Asn Pro Ile Gly Ser Ile Ala Ala Met Cys Gly Met Ser Pro Met
            340                 345                 350
Val Ser Ala Leu Ser Leu Asn Pro Ser Asn Glu Ser Ser Pro Ile Tyr
        355                 360                 365
Ile Leu Pro Arg Phe Ser Asp Lys Tyr Ser Arg Gly Gly Arg Asp Trp
    370                 375                 380
Arg Val Pro Val Glu Val Ser Ser Gln Leu Trp Leu Ile His Ser Gly
385                 390                 395                 400
Asn Ala Tyr Glu Thr Arg Glu Asp Asn Gly Asp Leu Lys Ile Gln Ile
                405                 410                 415
Gln Ala Ser Ala Cys Ser Tyr Arg Trp Phe Asp Phe Gln Lys Met Phe
            420                 425                 430
Gly Tyr Asp Trp Gln Ser Asn Lys Leu Asp Pro Ser Val Met Asn Leu
        435                 440                 445
Asn Arg Gly Asp Asp Lys Leu Leu Pro His Leu Val Lys Val Ser Met
    450                 455                 460
Thr Leu Asp Ser Thr Gly Asn Cys Asn Ser Cys Asp Val Glu Pro Leu
465                 470                 475                 480
Asn Gly Trp Asn Lys Pro Ser Asp Phe Pro Val Ile Asn Ser Ser Trp
                485                 490                 495
Ser Gly Lys Lys Asn Lys Tyr Met Tyr Ser Ala Ala Ser Ser Gly Thr
            500                 505                 510
Arg Ser Glu Leu Pro His Phe Pro Phe Asp Met Val Val Lys Phe Asp
        515                 520                 525
Leu Asp Ser Asn Leu Val Arg Thr Trp Ser Thr Gly Ala Arg Arg Phe
    530                 535                 540
Val Gly Glu Pro Met Phe Val Pro Lys Asn Ser Val Glu Glu Gly Glu
545                 550                 555                 560
Glu Glu Asp Asp Gly Tyr Ile Val Val Glu Tyr Ala Val Ser Val
                565                 570                 575
Glu Arg Cys Tyr Leu Val Ile Leu Asp Ala Lys Lys Ile Gly Glu Ser
            580                 585                 590
Asp Ala Val Val Ser Arg Leu Glu Val Pro Arg Asn Leu Thr Phe Pro
        595                 600                 605
Met Gly Phe His Gly Leu Trp Ala Ser Asp
    610                 615
```

<210> SEQ ID NO 5
<211> LENGTH: 3109
<212> TYPE: DNA
<213> ORGANISM: Oryza sativa

<400> SEQUENCE: 5

| | | | | | |
|---|---|---|---|---|---|
| atgtctcccg | ctatgctgca | ggcgtcgtcg | ctgtgcgtat | ccgcggcgct | gtcaggcgcc | 60 |
| gcgagccggc | cgggccgcct | ggccagccag | gggcaccagg | gcaagcgggc | cgtggcgcag | 120 |
| cctctcgcgg | ctagcgccgt | gacggaggca | gcgccgcccg | cgccggtcgt | cgcgccgccg | 180 |
| gcccgccccg | tcgacgcccc | gcggcgccgt | ggcggacgtg | gcggcggcgg | aggcggcggc | 240 |
| gagctcgtgg | cgtggaagag | tgtacggcag | gagaggtggg | agggtgcgct | cgaggtggac | 300 |
| ggagagctgc | ctctctggct | ggtgggttaa | gcctcctact | gattgcaaat | ctccctaaat | 360 |
| atgacttgat | ttggctttg | ccttctctcc | accctaatta | agtattcatg | aacacaccat | 420 |
| aacctcagca | ttttataaga | tctgccggtg | gtcaagctaa | ggctagccgt | gcattttca | 480 |
| ttcaagaatg | cgaatctttt | ctgttatttt | gattcaaagg | tttcccagta | ctccatatcg | 540 |
| ctttcttgag | atcatctata | aactaaagat | ccttttgaac | atcttagtaa | aaaagcatgc | 600 |
| acaacatctt | cccacacatt | gagaaatacg | aaaggcactt | tctggaccac | atcactgtgc | 660 |
| aacaaatcct | ttataattaa | cctaaccatt | tcatcttgt | agcatctcct | tgattagtgc | 720 |
| aggctaaccg | ctgacctaga | gcacatatat | gcatatagcc | ccagaagggt | cctaaaaagg | 780 |
| taccagcttt | ggccacgtac | ctagcatatt | tttaccagca | gtatctaaca | cgccagggta | 840 |
| tattacttgc | cgactgtcat | ttttaatttc | cactgtgcca | gcagttgctg | aagcactcac | 900 |
| ccaaatcttc | agtaatttga | tcgacaaaga | ggagggcgac | actaacttac | cctatgctgg | 960 |
| cctagcgaaa | aggagatggc | atcttggcac | tcacgatgct | tgcggggaac | acaacatata | 1020 |
| tacccagatt | ctctgctcac | ccctagcttc | gatcggcgac | aacaatggca | tcactgtctt | 1080 |
| gtggttgcag | ttttgttgca | ccccgcaact | ctctgaaaac | aaaagtcaaa | accttggtc | 1140 |
| tccctaact | ccaagtgatc | ttatcactgt | tcttgccaat | tttgatagtg | acttgatttg | 1200 |
| aggaattaat | acaggtgtac | atgtagtata | atattgttgt | aactttgtag | ttacactcac | 1260 |
| taagctatgg | ataatacaat | cgtttcagct | aattaaaaat | gcaatcttct | gaggtaagct | 1320 |
| cgtggataga | ttaatttgtc | ggtcgttaat | tagaggtgga | cggatttgtc | gacgtgctgc | 1380 |
| aaatgattga | tcggatcgat | gcatacttgc | tgcaggatgg | cacgtacctg | aggaacggcc | 1440 |
| cgggactatg | gaacctcggc | gactacggct | tccggcacct | gttcgacggc | tacgcgacgc | 1500 |
| tggtgcgcgt | ctcgttccgc | ggcggccgcg | ccgtgggcgc | gcaccggcag | atcgagtcgg | 1560 |
| aggcgtacaa | ggcggcgcgc | gcgcacggca | aggtgtgcta | ccgcgagttc | tcggaggtgc | 1620 |
| ccaagccgga | caacttcctg | tcctacgtcg | gccagctggc | gaccctcttc | tcgggctcgt | 1680 |
| cgctcaccga | caactccaac | accgcgtcg | tcatgctcgg | cgacgccgc | gtgctctgcc | 1740 |
| tcacggagac | catcaagggc | tccatccagg | tcgacccgga | cacgctcgac | acggtcggca | 1800 |
| agttccagta | cacggacaag | ctgggcgggc | tgatccactc | ggcgcacccg | atcgtgaccg | 1860 |
| acaccgagtt | ctggacgctg | atccccgacc | tgatccggcc | cggctacgtg | gtggcgagga | 1920 |
| tggacgccgg | tagcaacgag | aggcagttcg | tcggcagggt | ggactgccgc | ggcgggccgg | 1980 |
| cgccagggtg | ggtgcactcg | ttcccccgtca | ccgagcacta | cgtcgtcgtg | ccggagatgc | 2040 |
| cgctccgcta | ctgcgccaag | aacctcctcc | gcgccgagcc | cacgccgctg | tacaagttcg | 2100 |
| agtggcacct | cgagtccggc | agctacatgc | acgtcatgtg | caaggccagc | ggcaagattg | 2160 |
| taagccatca | tcaatcgctg | ccgcccgtag | tgcgttcccg | ttttgcctat | ttaattggtt | 2220 |

-continued

```
gggtgatcta atgatgatat ttgtcgggac gatggccaac cgaaggtggc gagcgtggag    2280
gtgccgccgt tcgtgacgtt ccacttcatc aacgcgtacg aggagacgga cgaggagggg    2340
cgcgtgacgg cgatcatcgc cgactgctgc gagcacaacg ccaacaccgc catcctcgac    2400
aagctccgcc tccacaacct ccgctcctcc agcggccagg acgtcctccc cgacgccagg    2460
tacgtacaca cacgagccac acgacgacgt cccgccgtca atttgctacg ctacgcatgc    2520
acgtatgcac gatggatgac ggggaacacc atgtgtaggg tggggcggtt caggatcccc    2580
ctggacggga gccagttcgg cgagctggag acggcgctgg acccggagga gcacgggcgg    2640
ggcatggaca tgtgcagcat caacccggcg cacgtcggca gggagtaccg gtacgcctac    2700
gcctgcggcg cccgccggcc gtgcaacttc cccaacacgc tcaccaaggt cgacctggtg    2760
gagaggacgg ccaagaactg cacgaggag gcctccgtgc cgtccgagcc cttcttcgtg     2820
ccacgccccg cgccaccga ggaagacgac ggttagtgtc accatctctc ctcgttggct     2880
gcgtatacgt acgtcttggc tttgcctcgt ttcgtttgta ataacttgac caactctgtt    2940
attgatggca ggcgtggcga tatcgatggt gagcgccaag gacgggtcgg gctatgcgct    3000
ggtgctggac ggcaagacgt tcgaggaggt cgcgcgggcc aagttcccgt acgggctgcc    3060
ctacggcttg cactgctgct gggtgcccag gaaaaggaac agcaagtaa                3109
```

<210> SEQ ID NO 6
<211> LENGTH: 569
<212> TYPE: PRT
<213> ORGANISM: Oryza sativa

<400> SEQUENCE: 6

```
Met Ser Pro Ala Met Leu Gln Ala Ser Ser Leu Cys Val Ser Ala Ala
1               5                   10                  15

Leu Ser Gly Ala Ala Ser Arg Pro Gly Arg Leu Ala Ser Gln Gly His
                20                  25                  30

Gln Gly Lys Arg Ala Val Ala Gln Pro Leu Ala Ala Ser Ala Val Thr
            35                  40                  45

Glu Ala Ala Pro Pro Ala Pro Val Val Ala Pro Pro Ala Arg Pro Val
        50                  55                  60

Asp Ala Pro Arg Arg Arg Gly Arg Gly Gly Gly Gly Gly Gly
65                  70                  75                  80

Glu Leu Val Ala Trp Lys Ser Val Arg Gln Glu Arg Trp Glu Gly Ala
                85                  90                  95

Leu Glu Val Asp Gly Glu Leu Pro Leu Trp Leu Asp Gly Thr Tyr Leu
            100                 105                 110

Arg Asn Gly Pro Gly Leu Trp Asn Leu Gly Asp Tyr Gly Phe Arg His
        115                 120                 125

Leu Phe Asp Gly Tyr Ala Thr Leu Val Arg Val Ser Phe Arg Gly Gly
    130                 135                 140

Arg Ala Val Gly Ala His Arg Gln Ile Glu Ser Glu Ala Tyr Lys Ala
145                 150                 155                 160

Ala Arg Ala His Gly Lys Val Cys Tyr Arg Glu Phe Ser Glu Val Pro
                165                 170                 175

Lys Pro Asp Asn Phe Leu Ser Tyr Val Gly Gln Leu Ala Thr Leu Phe
            180                 185                 190

Ser Gly Ser Ser Leu Thr Asp Asn Ser Asn Thr Gly Val Val Met Leu
        195                 200                 205

Gly Asp Gly Arg Val Leu Cys Leu Thr Glu Thr Ile Lys Gly Ser Ile
    210                 215                 220
```

```
Gln Val Asp Pro Asp Thr Leu Asp Thr Val Gly Lys Phe Gln Tyr Thr
225                 230                 235                 240

Asp Lys Leu Gly Gly Leu Ile His Ser Ala His Pro Ile Val Thr Asp
            245                 250                 255

Thr Glu Phe Trp Thr Leu Ile Pro Asp Leu Ile Arg Pro Gly Tyr Val
        260                 265                 270

Val Ala Arg Met Asp Ala Gly Ser Asn Glu Arg Gln Phe Val Gly Arg
    275                 280                 285

Val Asp Cys Arg Gly Gly Pro Ala Pro Gly Trp Val His Ser Phe Pro
290                 295                 300

Val Thr Glu His Tyr Val Val Pro Glu Met Pro Leu Arg Tyr Cys
305                 310                 315                 320

Ala Lys Asn Leu Leu Arg Ala Glu Pro Thr Pro Leu Tyr Lys Phe Glu
            325                 330                 335

Trp His Leu Glu Ser Gly Ser Tyr Met His Val Met Cys Lys Ala Ser
        340                 345                 350

Gly Lys Ile Val Ala Ser Val Glu Val Pro Pro Phe Val Thr Phe His
    355                 360                 365

Phe Ile Asn Ala Tyr Glu Glu Thr Asp Glu Gly Arg Val Thr Ala
370                 375                 380

Ile Ile Ala Asp Cys Cys Glu His Asn Ala Asn Thr Ala Ile Leu Asp
385                 390                 395                 400

Lys Leu Arg Leu His Asn Leu Arg Ser Ser Ser Gly Gln Asp Val Leu
            405                 410                 415

Pro Asp Ala Arg Val Gly Arg Phe Arg Ile Pro Leu Asp Gly Ser Gln
        420                 425                 430

Phe Gly Glu Leu Glu Thr Ala Leu Asp Pro Glu Glu His Gly Arg Gly
    435                 440                 445

Met Asp Met Cys Ser Ile Asn Pro Ala His Val Gly Arg Glu Tyr Arg
450                 455                 460

Tyr Ala Tyr Ala Cys Gly Ala Arg Arg Pro Cys Asn Phe Pro Asn Thr
465                 470                 475                 480

Leu Thr Lys Val Asp Leu Val Glu Arg Thr Ala Lys Asn Trp His Glu
            485                 490                 495

Glu Gly Ser Val Pro Ser Glu Pro Phe Phe Val Pro Arg Pro Gly Ala
        500                 505                 510

Thr Glu Glu Asp Asp Gly Val Ala Ile Ser Met Val Ser Ala Lys Asp
    515                 520                 525

Gly Ser Gly Tyr Ala Leu Val Leu Asp Gly Lys Thr Phe Glu Glu Val
530                 535                 540

Ala Arg Ala Lys Phe Pro Tyr Gly Leu Pro Tyr Gly Leu His Cys Cys
545                 550                 555                 560

Trp Val Pro Arg Lys Arg Asn Ser Lys
            565
```

<210> SEQ ID NO 7
<211> LENGTH: 3250
<212> TYPE: DNA
<213> ORGANISM: Arabidopsis thaliana

<400> SEQUENCE: 7
attcactaaa acttcattta cttcttgaa cttgtcttgt gccctctttc caatacactg   60
aaatccactt caaatatttt atttaataaa aagaaaagaa aagaaaaaaa ctctgccagg  120
atggcttctt tgatcacaac caaagcaatg atgagtcatc atcatgtttt gtcgtcaact  180

-continued

```
agaatcacta ctctttattc cgacaattcc atcggcgatc aacaaataaa aacaaaacct      240
caagtccctc accggttatt tgctcggagg atcttcggtg taaccagagc tgtaattaat      300
tcagcggcac cgtctccgtt gccggagaaa gagaaggtgg aaggtgagag acggtgtcat      360
gttgcgtgga caagtgtaca acaagagaat tgggaggtg aacttactgt ccaaggaaag       420
atacccactt ggctggtttg tcttttatc atttttctat attgctccaa atatataact       480
tatagctata ttcgtggaaa ttttatacaa atatgtatcg tgcacactaa acacactcac     540
actggcacat gcatatgtat ataatacaag acaaacccca ttcatcatgc attatttata     600
gttattctat atattacgta tacattttc tttccttata catgatttca ttactaagaa      660
agagtaagag ctatttgtcc aaaaaaaaaa aaaaaaaga aagaaagagt aagagcttag      720
gttagtacac catgttcgta tttatatatc aatatatgca gtgagaatca gaagaaatag    780
agaacaaagg ttcagatttt aataaagaag atatgctagt ttccaaaaag atatatatgc    840
acatatatat tattagtcta ggttatatat gttctattat ttctacaagt tttgttttct   900
ctattatttt tacaagacta caagttctaa actggtcata ggcatggttg gtacttctac  960
aagttgtact cttgaccatt gcaatctaaa atcagcatac aatcatgttt cataaaatac  1020
accaacaatc atgtaccaaa aaatctatttt tttttagttt ttgataaatt aataatattt  1080
ttactaaaac aaaactccat aaacaaaatc atcaaaattt ttaaaaaaag aagtaaaaat   1140
gagacaagaa aactaatgat ttaaaatgac atgcagaatg gtacgtacct aagaaacggt   1200
cctggtctat ggaacattgg agaccacgat ttccggcatc tcttcgacgg ctactccaca  1260
ctcgtcaagc ttcaattcga tggcggtcgt atattcgccg cccaccgtct ccttgaatcc  1320
gacgcttaca aagccgccaa gaaacacaat aggctttgtt accgtgaatt ctccgagact  1380
ccaaaatcgg tgatcataaa caaaaccct ttctccggga tcggagaaat cgtcaggctt    1440
ttctccggag agtctttaac ggacaacgcc aacaccggag tgatcaaact cggtgacggg   1500
cgggtcatgt gtctgacgga gactcaaaaa ggatcgattt tagtcgacca tgagacgcta   1560
gagacgatcg ggaaatttga gtacgacgac gtattgtccg atcatatgat ccaatcagcg    1620
catccgatag tgacggagac ggagatgtgg acgttgatac cggatttggt taaaccgggt    1680
tatcgggtcg tgaggatgga agccgggtcg aataaaagag aggttgtggg gcgggtgagg   1740
tgtcgaagtg ggtcgtgggg acccggttgg gtccattcgt ttgcggtgac ggagaattat   1800
gttgtaatac cggaaatgcc cctgagatat tcggtgaaga atcttcttag agctgagccg   1860
acgccacttt acaagttcga gtggtgtccc caagacggag cttttattca tgtcatgtcc   1920
aaactcaccg gagaagtcgt aagtgatact tactttatac agtcaatggt ctttcaaatt   1980
tttaggtttt tattggttat agagttatat atatagtact atatatagta gatcatagtt   2040
tatggatggt ttttctttag ttaactataa caacaaaata ataggattct tgataatgta   2100
tatcattgga aattaaccat gtaacagaat attgtttgat ggttttttg gtcatttgat    2160 ttgaatatac ataaaaccat aacgttatat atggttaaag gtggctagcg tggaggttcc   2220
agcatacgta acgtttcact tcataaacgc gtatgaagaa gataaaaatg gcgatggaaa  2280
agcgacggtc atcattgcag attgttgtga acacaacgcc gatactcgga tactcgatat   2340
gctccgtctc gataccctac gttcttccca tggtcacgac gttttacccg atgctaggta   2400
atgtatataa gggttactac tcaatactca tcacctacat ttttcagttt tgattatagc   2460
tggattaatg taatcttatg ttaggatcgg agagattcagg ataccattgg acgggagcaa  2520
atacgggaaa ctagagacag ccgtggaggc agagaagcat gggagagcga tggatatgtg   2580
```

-continued

```
cagcatcaat cctttgtatt tgggtcaaaa ataccgttac gtttatgcat gcggtgctca    2640
acgaccttgt aacttcccca atgctctctc caaggtaact tacatacccc aaactatcgg    2700
tttccaatat tcaatcgttt tgaatgaacc ttttgataat tgtatgagac aggttgatat    2760
tgtggagaag aaagtgaaga actggcacga gcatggtatg ataccatctg aaccattctt    2820
cgtgcctcga cccggtgcaa cccatgagga tgatggttag ttaaaaattc tttagatctt    2880
attggtcttt cttcgacgtg agtttaatag ttttggtttt gtgaaggagt ggtgatatcg    2940
atagtaagtg aagaaaatgg aggaagcttt gcaatcttgc ttgatgggag ctcctttgaa    3000
gaaatagcaa gagccaagtt tccctatggc cttccttatg gcttgcatgg ttgctggatc    3060
cccaaagatt aactacaaag tctcaacaaa gataccttca ttatacaaaa cacaacatat    3120
gtataattaa taccctctgt gcaggttttg taaattgttg tcccttatat atgctttttg    3180
tctatatatg tgatgtacaa aaccaaaata aaaggaacgg attgtggtgg atacagttat    3240
taaaaattgc                                                          3250
```

<210> SEQ ID NO 8
<211> LENGTH: 570
<212> TYPE: PRT
<213> ORGANISM: Arabidopsis thaliana

<400> SEQUENCE: 8

```
Met Ala Ser Leu Ile Thr Thr Lys Ala Met Met Ser His His His Val
1               5                   10                  15

Leu Ser Ser Thr Arg Ile Thr Thr Leu Tyr Ser Asp Asn Ser Ile Gly
            20                  25                  30

Asp Gln Gln Ile Lys Thr Lys Pro Gln Val Pro His Arg Leu Phe Ala
        35                  40                  45

Arg Arg Ile Phe Gly Val Thr Arg Ala Val Ile Asn Ser Ala Ala Pro
    50                  55                  60

Ser Pro Leu Pro Glu Lys Glu Lys Val Glu Gly Glu Arg Arg Cys His
65                  70                  75                  80

Val Ala Trp Thr Ser Val Gln Gln Glu Asn Trp Glu Gly Glu Leu Thr
                85                  90                  95

Val Gln Gly Lys Ile Pro Thr Trp Leu Asn Gly Thr Tyr Leu Arg Asn
            100                 105                 110

Gly Pro Gly Leu Trp Asn Ile Gly Asp His Asp Phe Arg His Leu Phe
        115                 120                 125

Asp Gly Tyr Ser Thr Leu Val Lys Leu Gln Phe Asp Gly Gly Arg Ile
    130                 135                 140

Phe Ala Ala His Arg Leu Leu Glu Ser Asp Ala Tyr Lys Ala Ala Lys
145                 150                 155                 160

Lys His Asn Arg Leu Cys Tyr Arg Glu Phe Ser Glu Thr Pro Lys Ser
                165                 170                 175

Val Ile Ile Asn Lys Asn Pro Phe Ser Gly Ile Gly Glu Ile Val Arg
            180                 185                 190

Leu Phe Ser Gly Glu Ser Leu Thr Asp Asn Ala Asn Thr Gly Val Ile
        195                 200                 205

Lys Leu Gly Asp Gly Arg Val Met Cys Leu Thr Glu Thr Gln Lys Gly
    210                 215                 220

Ser Ile Leu Val Asp His Glu Thr Leu Glu Thr Ile Gly Lys Phe Glu
225                 230                 235                 240

Tyr Asp Asp Val Leu Ser Asp Met Ile Gln Ser Ala His Pro Ile
                245                 250                 255
```

```
Val Thr Glu Thr Glu Met Trp Thr Leu Ile Pro Asp Leu Val Lys Pro
                260                 265                 270

Gly Tyr Arg Val Val Arg Met Glu Ala Gly Ser Asn Lys Arg Glu Val
            275                 280                 285

Val Gly Arg Val Arg Cys Arg Ser Gly Ser Trp Gly Pro Gly Trp Val
        290                 295                 300

His Ser Phe Ala Val Thr Glu Asn Tyr Val Val Ile Pro Glu Met Pro
305                 310                 315                 320

Leu Arg Tyr Ser Val Lys Asn Leu Leu Arg Ala Glu Pro Thr Pro Leu
                325                 330                 335

Tyr Lys Phe Glu Trp Cys Pro Gln Asp Gly Ala Phe Ile His Val Met
            340                 345                 350

Ser Lys Leu Thr Gly Glu Val Val Ala Ser Val Glu Val Pro Ala Tyr
        355                 360                 365

Val Thr Phe His Phe Ile Asn Ala Tyr Glu Glu Asp Lys Asn Gly Asp
370                 375                 380

Gly Lys Ala Thr Val Ile Ile Ala Asp Cys Cys Glu His Asn Ala Asp
385                 390                 395                 400

Thr Arg Ile Leu Asp Met Leu Arg Leu Asp Thr Leu Arg Ser Ser His
                405                 410                 415

Gly His Asp Val Leu Pro Asp Ala Arg Ile Gly Arg Phe Arg Ile Pro
            420                 425                 430

Leu Asp Gly Ser Lys Tyr Gly Lys Leu Glu Thr Ala Val Glu Ala Glu
        435                 440                 445

Lys His Gly Arg Ala Met Asp Met Cys Ser Ile Asn Pro Leu Tyr Leu
450                 455                 460

Gly Gln Lys Tyr Arg Tyr Val Tyr Ala Cys Gly Ala Gln Arg Pro Cys
465                 470                 475                 480

Asn Phe Pro Asn Ala Leu Ser Lys Val Asp Ile Val Glu Lys Lys Val
                485                 490                 495

Lys Asn Trp His Glu His Gly Met Ile Pro Ser Glu Pro Phe Phe Val
            500                 505                 510

Pro Arg Pro Gly Ala Thr His Glu Asp Asp Gly Val Val Ile Ser Ile
        515                 520                 525

Val Ser Glu Glu Asn Gly Gly Ser Phe Ala Ile Leu Leu Asp Gly Ser
530                 535                 540

Ser Phe Glu Glu Ile Ala Arg Ala Lys Phe Pro Tyr Gly Leu Pro Tyr
545                 550                 555                 560

Gly Leu His Gly Cys Trp Ile Pro Lys Asp
                565                 570

<210> SEQ ID NO 9
<211> LENGTH: 2871
<212> TYPE: DNA
<213> ORGANISM: Arabidopsis thaliana

<400> SEQUENCE: 9
attaaactaa agaagagaga actttagagg ttagagagat gaagacgcaa catcaatggt      60
gggaagttct tgatccattc ttgacacaac acgaagctct tattgcattc ttgacttttg     120
cagcggttgt aattgtgatt tacttgtacc gaccctcctg gtccgtatgc aatgttcccg     180
gtccaaccgc tatgcctcta gttggtcact tgcccttgat ggctaagtat ggtcctgatg     240
tcttctccgt tcttgctaag caatatggcc ctatttttcag gtacctctcc tctctctctc     300
tctttattct gttttcggtg gctagagacc tagagtttag ttttttaagtt ttcgtgtcga     360
```

```
caaaaaaaaa cagttttagt taatttgttc ggtttaatgt aattttttggt ttatttgatt      420 tgattttctg tttagacttt agagtcagtt tgattttttaa aataaggaaa acaacttcat      480
gtaaatagtg ctttaattaa tatacaagta cttttttaaca tatataatta aaaaatataa      540 cttttttaatg aatttctgtt tatttataac ttcagtttca ttttttagtca tttgataata      600 atgaaaccaa tttaaccaaa agagataaat aattaagaaa acctaatgga aaaaaacatt      660
tataatttaa tgtagttttt gtattatttc atttgatttt cagtttattt taatttaaat      720
gatttataaa cacattatgt ttaattttgt ttaatcattt tggtttagtt tggtatatat      780
ggccatctct tatggttgtt atgactgagt gatgaacaca acaagtgtct aaaaaacaaa      840
atgaagacaa gtgatcatgt ccatttaaat taacaacaaa cagatttcag atggggaggc      900
aaccactgat aataatagca gaagcagagc tttgcagaga agttgggata aagaagttca      960
aagatcttcc aaacagaagc attccttccc caatctcagc ttctcctctt cacaagaaag     1020
gcctcttctt caccaggtac aatggtacat acatgctcta taaaactatg tatgtttttg     1080
tttctataac catttatgat tctttgacag ggacaagaga tggtctaaaa tgagaaacac     1140
catcctatct ctctatcagc cttcacattt aacaagtctt atccctacaa tgcatagttt     1200
catcacttct gctactcata atcttgattc taaaccgcga gatatcgttt tctccaacct     1260
cttcctcaaa cttaccactg atatcatcgg acaagcggct tttggagtcg acttcggtct     1320
ttccgggaag aaaccaatca aagatgtgga ggtgactgat ttcataaacc agcatgtcta     1380
ctctacaaca caactcaaga tggatttatc aggatcactc tctatcatct taggcttact     1440
gattccgatt cttcaagagc cgtttaggca ggtgttgaag aggataccgg gaacaatgga     1500
ctggagagtc gagaagacta atgcaagact gagtggacaa cttaatgaga ttgtgtcaaa     1560
gcgagccaag gaggctgaga ctgactcaaa agacttcttg tcattgattt tgaaagctcg     1620
agagtccgat cctttcgcca aaacatcttc acatcggat tatattagtg ctgtgactta     1680
tgagcatctt cttgctggct ctgcaaccac tgctttcaca ctatcctctg ttctttactt     1740
agtctctggt catcttgatg ttgagaaacg tctgcttcaa gaaattgacg ggtttgggaa     1800
ccgtgatctg atcccgactg ctcatgactt acaacacaag tttccatacc tcgatcaggt     1860
gcttcattag taacaaacaa aaaccgagaa gttgagtttc tgtgagagat tagaatcttt     1920
atgaatgttt tttatttgcc tcctttgtag gtcattaaag aggctatgag attctacatg     1980
gtttctcctt tggttgcaag ggaaactgct aaagaagtgg agataggagg ttatttactc     2040
ccaaaggtat attcaaaccc atcaagcgga ttagtccatt tacagtcagc acttgtaatc     2100
tattacttac cttgtggttg ttgcttaggg gacatgggtt tggttagcac taggagttct     2160
agcaaaggac cctaaaaact ttccagaacc ggagaagttc aagccggaaa gatttgatcc     2220
gaacggagaa gaggagaaac atagacatcc atacgctttc atcccattcg gtatcggtcc     2280
acgagcctgt gttggacaga gatttgccct gcaagagatc aaactcacat tactgcatct     2340
ctaccgtaat tacattttca gacattccct agaaatggag ataccactgc agcttgatta     2400
tggtataatt ctcagcttca agaacggggt taagctcaga accatcaaaa gattctgatt     2460
cttgaaacaa gtgaaataaa agcaagactg aaatttatat ttaaattcaa aactccaatg     2520
tagttccaaa ggaaaaagaa caattaacaa catacacaga tatctcacaa cacacaagac     2580
aacaacaagc tgttgaaact ccaatctaac aaggtcacat ttaacctctc ggcttctcga     2640
atcgagtagg aacaccgagt ggtttggaga aactaacaaa aggatctgag gaaggactag     2700
tcttcaattc ccctgtaaac attccagagt tcttcataaa ctgaaactca tccatagatt     2760
```

```
gcctgagacc gcggttagtt cttcgcttag cctttgtcga ttcagtcaag ctcatgtaac   2820
ttggcttgtg cttttttgct tgactgctag agttatctga aacaagtcca g            2871
```

<210> SEQ ID NO 10
<211> LENGTH: 439
<212> TYPE: PRT
<213> ORGANISM: Arabidopsis thaliana

<400> SEQUENCE: 10

```
Met Gly Arg Gln Pro Leu Ile Ile Ile Ala Glu Ala Glu Leu Cys Arg
1               5                   10                  15

Glu Val Gly Ile Lys Lys Phe Lys Asp Leu Pro Asn Arg Ser Ile Pro
            20                  25                  30

Ser Pro Ile Ser Ala Ser Pro Leu His Lys Lys Gly Leu Phe Phe Thr
        35                  40                  45

Arg Asp Lys Arg Trp Ser Lys Met Arg Asn Thr Ile Leu Ser Leu Tyr
    50                  55                  60

Gln Pro Ser His Leu Thr Ser Leu Ile Pro Thr Met His Ser Phe Ile
65                  70                  75                  80

Thr Ser Ala Thr His Asn Leu Asp Ser Lys Pro Arg Asp Ile Val Phe
                85                  90                  95

Ser Asn Leu Phe Leu Lys Leu Thr Thr Asp Ile Ile Gly Gln Ala Ala
            100                 105                 110

Phe Gly Val Asp Phe Gly Leu Ser Gly Lys Lys Pro Ile Lys Asp Val
        115                 120                 125

Glu Val Thr Asp Phe Ile Asn Gln His Val Tyr Ser Thr Thr Gln Leu
    130                 135                 140

Lys Met Asp Leu Ser Gly Ser Leu Ser Ile Ile Leu Gly Leu Leu Ile
145                 150                 155                 160

Pro Ile Leu Gln Glu Pro Phe Arg Gln Val Leu Lys Arg Ile Pro Gly
                165                 170                 175

Thr Met Asp Trp Arg Val Glu Lys Thr Asn Ala Arg Leu Ser Gly Gln
            180                 185                 190

Leu Asn Glu Ile Val Ser Lys Arg Ala Lys Glu Ala Thr Asp Ser
        195                 200                 205

Lys Asp Phe Leu Ser Leu Ile Leu Lys Ala Arg Glu Ser Asp Pro Phe
    210                 215                 220

Ala Lys Asn Ile Phe Thr Ser Asp Tyr Ile Ser Ala Val Thr Tyr Glu
225                 230                 235                 240

His Leu Leu Ala Gly Ser Ala Thr Thr Ala Phe Thr Leu Ser Ser Val
                245                 250                 255

Leu Tyr Leu Val Ser Gly His Leu Asp Val Glu Lys Arg Leu Leu Gln
            260                 265                 270

Glu Ile Asp Gly Phe Gly Asn Arg Asp Leu Ile Pro Thr Ala His Asp
        275                 280                 285

Leu Gln His Lys Phe Pro Tyr Leu Asp Gln Val Ile Lys Glu Ala Met
    290                 295                 300

Arg Phe Tyr Met Val Ser Pro Leu Val Ala Arg Glu Thr Ala Lys Glu
305                 310                 315                 320

Val Glu Ile Gly Gly Tyr Leu Leu Pro Lys Gly Thr Trp Val Trp Leu
                325                 330                 335

Ala Leu Gly Val Leu Ala Lys Asp Pro Lys Asn Phe Pro Glu Pro Glu
            340                 345                 350

Lys Phe Lys Pro Glu Arg Phe Asp Pro Asn Gly Glu Glu Glu Lys His
        355                 360                 365
```

```
Arg His Pro Tyr Ala Phe Ile Pro Phe Gly Ile Gly Pro Arg Ala Cys
        370                 375                 380

Val Gly Gln Arg Phe Ala Leu Gln Glu Ile Lys Leu Thr Leu Leu His
385                 390                 395                 400

Leu Tyr Arg Asn Tyr Ile Phe Arg His Ser Leu Glu Met Glu Ile Pro
                405                 410                 415

Leu Gln Leu Asp Tyr Gly Ile Ile Leu Ser Phe Lys Asn Gly Val Lys
            420                 425                 430

Leu Arg Thr Ile Lys Arg Phe
        435

<210> SEQ ID NO 11
<211> LENGTH: 4551
<212> TYPE: DNA
<213> ORGANISM: Oryza sativa

<400> SEQUENCE: 11
ttcaccccaa atccctcaac ggcagcaaga gagagaaaga agagagagag agagagagag      60
agagaggagt agacgtcgcc catggcggaa gaggaggagg tggaggaggg gaggtcctcg     120
tcgtcggcga tactgaccct gccggagccg ctgctgctgc acatcctgag cttcctgacg     180
gacgtgaggt ctcggcacag ggcggcgctg gcgtgcggga ggatgcgggc ggcggagcgg     240
gcgacgaggt cggagctctc gctgagggcc gacccgaggt cgccggggtt cctgttcctc     300
tcgcacgcgt tccgcttccc ggcgctggaa cacctcgacc tctcgctcgt ctcgccgtgg     360
gggcatccgc ttctctcctc cgtgccgccc tgcggcggcg gcggcggcgg cgcgccctcg     420
gcgtcgtcgt cgtcggggat gaacgtgtac caccccgagg cgatctccga gcagaacgcc     480
ttcatcgccg cccgcctcgc gggctgcttc ccggcggtga cctcgctcgc cgtctactgc     540 cgcgaccccca ccacgctcgc caacctcacc ccgcactggc aggcctccct ccgccgcgtc     600
aagctcgtgc gctggcacca cgcccgccc acccctcccg acggcgcgga tctcgagccg     660
ctgctggaga cctgcgccgc gctccgggag ctcgacctgt cggagttcta ctgctggacc     720
gaggacgtcg tgagggcgct caccacgcac ccttccgcca ccgcggcgct cacccacctc     780
gacctcggcc tcgccgccgc caccgacggc ttcaaatcct ccgagcttgg gccaatcgcg     840
gcctcctgcc ccaacctccg caagctcgtg gcgccatgct tgttcaaccc acggttcagc     900
gattgcgtcg gcgacgacgc gctgctctcg ctggccacca gctgcccgcg gctgaccgtc     960
ttgcggctca gcgagccgtt cgaggctgcg gccaacatcc agagggagga ggcggccatc    1020
accgttgcgg ggctagtcgc cttcttcgcg gcgctccccg cgctggagga tttcaccatg    1080
gatctccagc acaatgtgct ggaggccgcg cccgcgatgg aggcgcttgc ccgaaggtgc    1140
ccgcggatca agttcttgac cctgggttcc ttccagggc tgtgtaaggc ctcttggttg    1200
catcttgatg gtgttgcggt gtgcggtggg ctggagtcac tttacatgaa gaattgccag    1260
gatctcacgg atgccagcct tgcggcaatt ggccgtgggt gccggaggct tgctaagttc    1320
ggcatccatg gctgtgacct tgtcacttcg gctgggatca ggaggcttgc attcacgctt    1380
cggcctactc tcaaggaagt cactgtcttg cactgccggc ttctgcacac tgcagaatgt    1440
ctcactgctc taagtccgat ccgtgatcgc attgaaagtc ttgagatcaa ctgtgtctgg    1500
aacacaaccg aacaaccctg cagtgttgca atggcacca ccaccgaatg cgatcctgag    1560
gatgatgagc ttggtgaagt gtacgagtct gcagccaaga aatgtaggta catggaattt    1620
gatgatcttg gaagctggga gatgctcagg tcactctccc tatggttctc tgctggccag    1680
cttctctctc cgctcatttc tgctggtctc gatagctgtc ccgtgcttga ggagatctca    1740
```

| | |
|---|---|
| attaaggtgg agggtgattg ccggacatgc ccacgacctg ctccaagaac aattttttggc | 1800 |
| ttaagtgatc ttgcaggctt cccagtatta gccaagatga aattggacct cagtgaagct | 1860 |
| gtgggttatg cacttactgc accaacaggg cagatggatc tttcactatg ggagcgattt | 1920 |
| tatttgcatg gtatcgaatc actgcagact ttgtatgaat tggactactg gccgcccaa | 1980 |
| gacaaggatg tgcaccaccg gagcctgaca ttgccagccg tgggattgat ccaacgctgc | 2040 |
| gttggactca ggaagctttt catccatggc accacacatg agcacttcat gaccttcttc | 2100 |
| cttttcaattc caaacttgcg ggacatgcag ttgcgggagg actattatcc agccccagag | 2160 |
| aatgatctga tgttcacaga gatgcgggct gaatcttggc ttaggtttga ggtgcaactg | 2220 |
| aacagccggc aaattgatga ttagttatgt gggcacaaaa tggtttgaag ctgaatacag | 2280 |
| agatttatct ggatggtgcc attgctccac tgtgcaatgg caggggattc ctggtgagtt | 2340 |
| ggttatgatt atgggtggag tcgtgtgtat tgctgcagtg ccattgagga gagtagtata | 2400 |
| ctggcagcac ttggatctgt cagcaaagta accttctcca gttgcttttt tacccccttt | 2460 |
| ttgatgtaat aagagagttg ggtcggaaat gagatatttg caggagataa gattataaat | 2520 |
| taggcttcat ggaaaatttt ccaagaaaaa aaaacatttt gttttaaga tggtctgagt | 2580 |
| tgtgaacacc ggcaagagta attggcaaat tggcatggtt ctagcggttt gtaacatttg | 2640 |
| aactctgtaa acaaaagaaa aacgccactc gcttttctta tgcccctttgc ttcatgggtg | 2700 |
| aaagtggctc atctaatatt ggtcagtgtt ttactgtttt caatggatgg gcaacggagt | 2760 |
| tcagtactac tgcgatagga aactattttg atgtgtacat aacagctcta ttaatccaaa | 2820 |
| attatgtgcc tttgctcttt gagtttattt ctgtcccttt ccttttccat ttcatgcaca | 2880 |
| ggcttggtga caaatgggat ggcgtgtgca gatgtgcaag ccagttttgc atgtcattat | 2940 |
| cgggcatgtt gagttgcaac accggctaca acaaggttta ctttaataca cagcagtaag | 3000 |
| gatttaatct gatagaatgt tgaaaggttt tctctttttt atgcaggatt gaaagctgct | 3060 |
| ttagttttcca aggaacaacc aatcagttcc atcagaactg actaccacca tttgctgatt | 3120 |
| cgttctctgc agtgatcccc aatggagacc tggccttttgc ttcatctcat cctcaaactg | 3180 |
| tagcatgaca agaaagacgt gcggaacaag atcagcatca gaacatgaca aaaagatttt | 3240 |
| cgcactagaa gccggtttat ccaattcctc tgcttgcctc ttccattcag ctagttaaga | 3300 |
| taatgcgaga tcactggttt tgtcaaagca aatccagacg attcttggtg ccatggaaaa | 3360 |
| agaagtcgtc catgagtgag agagctctct tgtcctaatc catcagcaag ggcaataatg | 3420 |
| cttttttgat taagcagctg gaggcctcac aaaataatgc ttaagcaagt actactacag | 3480 |
| gattaaaagc tggcctctag aaggagtaga ttaggtagag gagaagcttc tcctttcctc | 3540 |
| ttttgccacg ttgaggctta ttgctcacat gattgtcaat caaccacgtc acacaagcac | 3600 |
| atacacacac ttattatttg ctcatagttt tagttatta tcaacatttg gcagatatgt | 3660 |
| gttggaaatt cagatgctcc ttgatgccat tttatcttgc tggtacatct gcataactcg | 3720 |
| ctcattacta tctgttgcaa tattattata catttggata tttaatgtgc tgatcgcttc | 3780 |
| ttgctaccta tctaatttca gaatgtcttg aaagcaaagc tggtgacagg agagatgtca | 3840 |
| tatgagcagg cagtcagttg cagccttgtg gttgcacctc cctttcctgc tgtcctcttt | 3900 |
| tttttgtttt ccctggtttc tcttcatcag aattaaagca gatattttg tggcggccgt | 3960 |
| ggatttccat tcatctgatg atcagctagt aatattctgc aagtgccttc cgatagaatt | 4020 |
| gagcgatgat tctgaggtca gatactcatc agatgctcga aggataagtg ggtttcagac | 4080 |
| gatgctgcaa aagatattag ccggcgagtg aggtgaggct actagcctac taggcttatc | 4140 |

-continued

```
gccttgtata aaactaaagg agtcagtaca gagacatcag gtaaagtcag catatgcagc    4200
tatccatcta tgcatgcatg caccaactgc aaagtaaagg taaaagtgaa agctttgtct    4260
tccaggtgta tggaagaaaa ttatccttgt gatggttatg caactcactc ttttgtttgc    4320
acccagatat gtcatattgg cttttttcacc atggtgtcaa ggttgatgtg aatgtgaatg    4380
tgattctact aatttgaggt catgtagagt aattaagtaa gcaaatggag cccgtcatgt    4440
cgtcatgcac tgacaaggat atagtcctat ggacctctat tttgattaat tggtggagaa    4500
aattcagagg aaaaatatgt gtgtgctgga atatgttggt atttttttttt t    4551
```

<210> SEQ ID NO 12
<211> LENGTH: 720
<212> TYPE: PRT
<213> ORGANISM: Oryza sativa

<400> SEQUENCE: 12

```
Met Ala Glu Glu Glu Val Glu Gly Arg Ser Ser Ser Ala
1               5                   10              15

Ile Leu Asp Leu Pro Glu Pro Leu Leu His Ile Leu Ser Phe Leu
                20                  25                  30

Thr Asp Val Arg Ser Arg His Arg Ala Ala Leu Ala Cys Gly Arg Met
            35                  40                  45

Arg Ala Ala Glu Arg Ala Thr Arg Ser Glu Leu Ser Leu Arg Gly Asp
        50                  55                  60

Pro Arg Ser Pro Gly Phe Leu Phe Leu Ser His Ala Phe Arg Phe Pro
65                  70                  75                  80

Ala Leu Glu His Leu Asp Leu Ser Leu Val Ser Pro Trp Gly His Pro
                85                  90                  95

Leu Leu Ser Ser Val Pro Pro Cys Gly Gly Gly Gly Gly Ala Pro
            100                 105                 110

Ser Ala Ser Ser Ser Ser Gly Met Asn Val Tyr His Pro Glu Ala Ile
        115                 120                 125

Ser Glu Gln Asn Ala Phe Ile Ala Ala Arg Leu Ala Gly Cys Phe Pro
    130                 135                 140

Ala Val Thr Ser Leu Ala Val Tyr Cys Arg Asp Pro Thr Thr Leu Ala
145                 150                 155                 160

Asn Leu Thr Pro His Trp Gln Ala Ser Leu Arg Arg Val Lys Leu Val
                165                 170                 175

Arg Trp His Gln Arg Pro Pro Thr Leu Pro Asp Gly Ala Asp Leu Glu
            180                 185                 190

Pro Leu Leu Glu Thr Cys Ala Ala Leu Arg Glu Leu Asp Leu Ser Glu
        195                 200                 205

Phe Tyr Cys Trp Thr Glu Asp Val Val Arg Ala Leu Thr Thr His Pro
    210                 215                 220

Ser Ala Thr Ala Ala Leu Thr His Leu Asp Leu Gly Leu Ala Ala Ala
225                 230                 235                 240

Thr Asp Gly Phe Lys Ser Ser Glu Leu Gly Pro Ile Ala Ala Ser Cys
                245                 250                 255

Pro Asn Leu Arg Lys Leu Val Ala Pro Cys Leu Phe Asn Pro Arg Phe
            260                 265                 270

Ser Asp Cys Val Gly Asp Asp Ala Leu Leu Ser Leu Ala Thr Ser Cys
        275                 280                 285

Pro Arg Leu Thr Val Leu Arg Leu Ser Glu Pro Phe Glu Ala Ala Ala
    290                 295                 300
```

```
Asn Ile Gln Arg Glu Glu Ala Ala Ile Thr Val Ala Gly Leu Val Ala
305                 310                 315                 320

Phe Phe Ala Ala Leu Pro Ala Leu Glu Asp Phe Thr Met Asp Leu Gln
            325                 330                 335

His Asn Val Leu Glu Ala Ala Pro Ala Met Glu Ala Leu Ala Arg Arg
                340                 345                 350

Cys Pro Arg Ile Lys Phe Leu Thr Leu Gly Ser Phe Gln Gly Leu Cys
                355                 360                 365

Lys Ala Ser Trp Leu His Leu Asp Gly Val Ala Val Cys Gly Gly Leu
            370                 375                 380

Glu Ser Leu Tyr Met Lys Asn Cys Gln Asp Leu Thr Asp Ala Ser Leu
385                 390                 395                 400

Ala Ala Ile Gly Arg Gly Cys Arg Arg Leu Ala Lys Phe Gly Ile His
                405                 410                 415

Gly Cys Asp Leu Val Thr Ser Ala Gly Ile Arg Arg Leu Ala Phe Thr
                420                 425                 430

Leu Arg Pro Thr Leu Lys Glu Val Thr Val Leu His Cys Arg Leu Leu
            435                 440                 445

His Thr Ala Glu Cys Leu Thr Ala Leu Ser Pro Ile Arg Asp Arg Ile
450                 455                 460

Glu Ser Leu Glu Ile Asn Cys Val Trp Asn Thr Thr Glu Gln Pro Cys
465                 470                 475                 480

Ser Val Ala Asn Gly Thr Thr Thr Glu Cys Asp Pro Glu Asp Asp Glu
                485                 490                 495

Leu Gly Glu Val Tyr Glu Ser Ala Ala Lys Lys Cys Arg Tyr Met Glu
            500                 505                 510

Phe Asp Asp Leu Gly Ser Trp Glu Met Leu Arg Ser Leu Ser Leu Trp
            515                 520                 525

Phe Ser Ala Gly Gln Leu Leu Ser Pro Leu Ile Ser Ala Gly Leu Asp
            530                 535                 540

Ser Cys Pro Val Leu Glu Glu Ile Ser Ile Lys Val Glu Gly Asp Cys
545                 550                 555                 560

Arg Thr Cys Pro Arg Pro Ala Pro Arg Thr Ile Phe Gly Leu Ser Asp
                565                 570                 575

Leu Ala Gly Phe Pro Val Leu Ala Lys Met Lys Leu Asp Leu Ser Glu
            580                 585                 590

Ala Val Gly Tyr Ala Leu Thr Ala Pro Thr Gly Gln Met Asp Leu Ser
            595                 600                 605

Leu Trp Glu Arg Phe Tyr Leu His Gly Ile Glu Ser Leu Gln Thr Leu
610                 615                 620

Tyr Glu Leu Asp Tyr Trp Pro Pro Gln Asp Lys Asp Val His His Arg
625                 630                 635                 640

Ser Leu Thr Leu Pro Ala Val Gly Leu Ile Gln Arg Cys Val Gly Leu
                645                 650                 655

Arg Lys Leu Phe Ile His Gly Thr Thr His Glu His Phe Met Thr Phe
                660                 665                 670

Phe Leu Ser Ile Pro Asn Leu Arg Asp Met Gly Leu Arg Glu Asp Tyr
            675                 680                 685

Tyr Pro Ala Pro Glu Asn Asp Leu Met Phe Thr Glu Met Arg Ala Glu
            690                 695                 700

Ser Trp Leu Arg Phe Glu Val Gln Leu Asn Ser Arg Gln Ile Asp Asp
705                 710                 715                 720
```

```
<210> SEQ ID NO 13
<211> LENGTH: 2329
<212> TYPE: DNA
<213> ORGANISM: Arabidopsis thaliana

<400> SEQUENCE: 13
atctcctctc ttgtagattt gccgcttctc atggcttcca ctactctctc cgacctccct      60
gacgtcatct tatccaccat ttcctctctc gtatccgatt cccgagctcg caactctctc     120
tccctcgtct ctcacaaatt cctcgctctc gaacgatcca ctcgctctca cctcactatc     180
cgtggcaacg ctcgtgatct ctccctcgtc cccgactgtt tccgatcaat ctcacatctc     240
gatctctctt tcctctcccc atggggtcac actcttctcg cttctctccc aatcgatcac     300
cagaaccttc tcgctctccg tctcaaattc tgtttcccctt tcgtcgagtc tctaaacgtc     360
tacacacgat ctccgagctc tctcgagctt ctacttcctc aatggccgag aattcgccac     420
atcaagctcc tccgatggca tcaacgagct tctcagatcc ctaccggtgg cgattttgtt     480 cctattttg aacactgtgg tggtttcctt gagtctttag atctctccaa cttctatcac     540
tggactgaag acttacctcc tgtgcttctc cgctatgctg acgtggcggc gaggcttaca     600
cggttagatc tcttgacggc gtcgttcacc gagggataca aatcaagcga aatcgttagt     660
atcaccaaat cttgccctaa tttgaagact tttcgtgtag cttgtacgtt tgatccgaga     720
tactttgaat tcgtcggaga cgagactctc tccgccgtag ctaccagttc ccctaagtta     780
acgcttctac acatggtgga cacagcttcg ttggcgaatc ctagagctat tccaggtacg     840
gaagctggag attcagctgt cacggcgggg acgctaattg aagttttctc aggtttaccg     900
aatctagagg agctggttct tgacgtagga aaggatgtga agcatagtgg tgtagcttta     960
gaggcattga attctaaatg caagaagtta agagtattga agctaggaca gttccaaggt    1020
gtttgctctg ctacagaatg gaggaggctc gacggtgtgg cttttatgtgg aggattgcag    1080 tcgttgtcga ttaagaattc cggcgatttg actgatatgg gtttggtggc tatagggaga    1140
ggatgttgta agttgactac gtttgagatt caagggtgtg agaatgtaac agtggatgga    1200
ctaagaacaa tggttagtct tcggagtaag actttgactg atgtgagaat ctcttgctgc    1260
aagaatcttg acacagctgc ttcttttaaag gcaattgagc cgatttgtga tcggatcaag    1320
agactgcata tagactgtgt gtggtctggt tcagaggacg aggaggtaga aggaagagtg    1380
gaaactagtg aggctgacca cgaagaggag gatgatggtt acgagaggag ccagaagagg    1440
tgcaagtatt cattcgagga agaacactgc tcaactagtg atgtgaatgg attctgttct    1500
gaagatagag tatgggagaa actggagtat ctatctttat ggatcaatgt tggagaattt    1560
ttgacgccat tacctatgac aggactagat gactgtccga atttggaaga gattaggatc    1620
aagatagaag gagattgcag aggtaaacgc aggccagccg agccagagtt tgggttaagt    1680
tgtctcgctc tctacccaaa gctctcaaag atgcagttag attgcgggga cacaatcggt    1740
ttcgcactga ccgcaccgcc aatgcagatg gatttgagtt tatgggaaag attcttcttg    1800
accggaattg gaagcttgag cttgagcgag cttgattatt ggccaccaca ggatagagat    1860
gttaaccaga ggagtctctc gcttcctgga gcaggtctgt tacaagagtg cctgactttg    1920
aggaagctgt tcatccatgg aacagctcat gagcatttca tgaacttttt gttgagaatc    1980
ccaaacttaa gggatgtaca gcttagagca gactattatc cggcgccgga gaacgatatg    2040
agcacagaga tgagagttgg ttcgtgtagc cgattcgagg accaattgaa cagccgcaac    2100
atcattgact gaaacttgaa gagtgagtta cctacactat tatatctgta ttgacttcag    2160
aaactggtcc atttttatttg tatggtcaag agtgttttgt atatgtttgt aagaggaaag    2220
```

```
gacaaagact ataatttgcg atgattaatg atatcataaa acaataatcc atttttataa    2280
atgataaaac tcaaatgaag aagccggaga gatctggagt acaaactca               2329
```

<210> SEQ ID NO 14
<211> LENGTH: 693
<212> TYPE: PRT
<213> ORGANISM: Arabidopsis thaliana

<400> SEQUENCE: 14

```
Met Ala Ser Thr Thr Leu Ser Asp Leu Pro Asp Val Ile Leu Ser Thr
1               5                   10                  15

Ile Ser Ser Leu Val Ser Asp Ser Arg Ala Arg Asn Ser Leu Ser Leu
            20                  25                  30

Val Ser His Lys Phe Leu Ala Leu Glu Arg Ser Thr Arg Ser His Leu
        35                  40                  45

Thr Ile Arg Gly Asn Ala Arg Asp Leu Ser Leu Val Pro Asp Cys Phe
    50                  55                  60

Arg Ser Ile Ser His Leu Asp Leu Ser Phe Leu Ser Pro Trp Gly His
65                  70                  75                  80

Thr Leu Leu Ala Ser Leu Pro Ile Asp His Gln Asn Leu Leu Ala Leu
                85                  90                  95

Arg Leu Lys Phe Cys Phe Pro Phe Val Glu Ser Leu Asn Val Tyr Thr
            100                 105                 110

Arg Ser Pro Ser Ser Leu Glu Leu Leu Leu Pro Gln Trp Pro Arg Ile
        115                 120                 125

Arg His Ile Lys Leu Leu Arg Trp His Gln Arg Ala Ser Gln Ile Pro
    130                 135                 140

Thr Gly Gly Asp Phe Val Pro Ile Phe Glu His Cys Gly Gly Phe Leu
145                 150                 155                 160

Glu Ser Leu Asp Leu Ser Asn Phe Tyr His Trp Thr Glu Asp Leu Pro
                165                 170                 175

Pro Val Leu Leu Arg Tyr Ala Asp Val Ala Ala Arg Leu Thr Arg Leu
            180                 185                 190

Asp Leu Leu Thr Ala Ser Phe Thr Glu Gly Tyr Lys Ser Ser Glu Ile
        195                 200                 205

Val Ser Ile Thr Lys Ser Cys Pro Asn Leu Lys Thr Phe Arg Val Ala
    210                 215                 220

Cys Thr Phe Asp Pro Arg Tyr Phe Glu Phe Val Gly Asp Glu Thr Leu
225                 230                 235                 240

Ser Ala Val Ala Thr Ser Ser Pro Lys Leu Thr Leu Leu His Met Val
                245                 250                 255

Asp Thr Ala Ser Leu Ala Asn Pro Arg Ala Ile Pro Gly Thr Glu Ala
            260                 265                 270

Gly Asp Ser Ala Val Thr Ala Gly Thr Leu Ile Glu Val Phe Ser Gly
        275                 280                 285

Leu Pro Asn Leu Glu Glu Leu Val Leu Asp Val Gly Lys Asp Val Lys
    290                 295                 300

His Ser Gly Val Ala Leu Glu Ala Leu Asn Ser Lys Cys Lys Lys Leu
305                 310                 315                 320

Arg Val Leu Lys Leu Gly Gln Phe Gln Gly Val Cys Ser Ala Thr Glu
                325                 330                 335

Trp Arg Arg Leu Asp Gly Val Ala Leu Cys Gly Gly Leu Gln Ser Leu
            340                 345                 350

Ser Ile Lys Asn Ser Gly Asp Leu Thr Asp Met Gly Leu Val Ala Ile
        355                 360                 365
```

-continued

Gly Arg Gly Cys Cys Lys Leu Thr Thr Phe Glu Ile Gln Gly Cys Glu
            370                 375                 380

Asn Val Thr Val Asp Gly Leu Arg Thr Met Val Ser Leu Arg Ser Lys
385                 390                 395                 400

Thr Leu Thr Asp Val Arg Ile Ser Cys Cys Lys Asn Leu Asp Thr Ala
                405                 410                 415

Ala Ser Leu Lys Ala Ile Glu Pro Ile Cys Asp Arg Ile Lys Arg Leu
                420                 425                 430

His Ile Asp Cys Val Trp Ser Gly Ser Glu Asp Glu Val Glu Gly
                435                 440                 445

Arg Val Glu Thr Ser Glu Ala Asp His Glu Glu Asp Asp Gly Tyr
    450                 455                 460

Glu Arg Ser Gln Lys Arg Cys Lys Tyr Ser Phe Glu Glu His Cys
465                 470                 475                 480

Ser Thr Ser Asp Val Asn Gly Phe Cys Ser Glu Asp Arg Val Trp Glu
                485                 490                 495

Lys Leu Glu Tyr Leu Ser Leu Trp Ile Asn Val Gly Glu Phe Leu Thr
                500                 505                 510

Pro Leu Pro Met Thr Gly Leu Asp Asp Cys Pro Asn Leu Glu Glu Ile
                515                 520                 525

Arg Ile Lys Ile Glu Gly Asp Cys Arg Gly Lys Arg Arg Pro Ala Glu
                530                 535                 540

Pro Glu Phe Gly Leu Ser Cys Leu Ala Leu Tyr Pro Lys Leu Ser Lys
545                 550                 555                 560

Met Gln Leu Asp Cys Gly Asp Thr Ile Gly Phe Ala Leu Thr Ala Pro
                565                 570                 575

Pro Met Gln Met Asp Leu Ser Leu Trp Glu Arg Phe Phe Leu Thr Gly
                580                 585                 590

Ile Gly Ser Leu Ser Leu Ser Glu Leu Asp Tyr Trp Pro Pro Gln Asp
                595                 600                 605

Arg Asp Val Asn Gln Arg Ser Leu Ser Leu Pro Gly Ala Gly Leu Leu
                610                 615                 620

Gln Glu Cys Leu Thr Leu Arg Lys Leu Phe Ile His Gly Thr Ala His
625                 630                 635                 640

Glu His Phe Met Asn Phe Leu Leu Arg Ile Pro Asn Leu Arg Asp Val
                645                 650                 655

Gln Leu Arg Ala Asp Tyr Tyr Pro Ala Pro Glu Asn Asp Met Ser Thr
                660                 665                 670

Glu Met Arg Val Gly Ser Cys Ser Arg Phe Glu Asp Gln Leu Asn Ser
                675                 680                 685

Arg Asn Ile Ile Asp
        690

<210> SEQ ID NO 15
<211> LENGTH: 18
<212> TYPE: DNA
<213> ORGANISM: Artificial
<220> FEATURE:
<223> OTHER INFORMATION: primer

<400> SEQUENCE: 15
ttggctttgc ctcgtttc                                                18

<210> SEQ ID NO 16
<211> LENGTH: 19
<212> TYPE: DNA
<213> ORGANISM: Artificial

-continued

```
<220> FEATURE:
<223> OTHER INFORMATION: primer

<400> SEQUENCE: 16
agcctccact tgtactgtg                                                    19

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
actctctccg acctccctga cg                                                22

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
aaacaccttg gaactgtcct agc                                               23

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
tgagactaga gaggataacg gc                                                22

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
aacatctctc caccgaaacc gc                                                22

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
cttaggttag tacaccatgt tcg                                               23

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
gtctccgtca ctatcggatg cgc                                               23
```

```
<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
catgtcatgt ccaaactcac cg                                          22

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
agtttcccgt atttgctccc g                                           21

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
ctgtacaagt tcgagtggca cc                                          22

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
cctcgtccgt ctcctcgtac                                             20

<210> SEQ ID NO 27
<211> LENGTH: 20
<212> TYPE: DNA
<213> ORGANISM: Artificial
<220> FEATURE:
<223> OTHER INFORMATION: TaqMan probe

<400> SEQUENCE: 27
caaggccagc ggcaagattg                                             20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
aaggtcacca ggctcaggaa g                                           21

<210> SEQ ID NO 29
<211> LENGTH: 20
<212> TYPE: DNA
<213> ORGANISM: Artificial
<220> FEATURE:
<223> OTHER INFORMATION: primer
```

```
<400> SEQUENCE: 29
gatcgaagtg gttggccatg                                              20

<210> SEQ ID NO 30
<211> LENGTH: 19
<212> TYPE: DNA
<213> ORGANISM: Artificial
<220> FEATURE:
<223> OTHER INFORMATION: TaqMan probe

<400> SEQUENCE: 30
caacaacgac tgcggcgcg                                               19
```